United States Patent
Techasakul et al.

(10) Patent No.: US 10,889,566 B2
(45) Date of Patent: Jan. 12, 2021

(54) DERIVATIVES AND COMPOSITION OF QUINOLINE AND NAPHTHYRIDINE

(71) Applicants: CHULABHORN FOUNDATION, Bangkok (TH); KASETSART UNIVERSITY, Bangkok (TH); SRINAKHARINWIROT UNIVERSITY, Bangkok (TH)

(72) Inventors: Supanna Techasakul, Bangkok (TH); Arthit Makarasen, Bangkok (TH); Nanthawan Reuk-Ngam, Bangkok (TH); Panita Khlaychan, Bangkok (TH); Mayuso Kuno, Bangkok (TH); Supa Hannongbua, Bangkok (TH)

(73) Assignees: Chulabhorn Foundation, Bangkok (TH); Kasetsart University, Bangkok (TH); Srinakharinwirot university, Bangkok (TH)

( * ) Notice: Subject to any disclaimer, the term of this patent is extended or adjusted under 35 U.S.C. 154(b) by 0 days.

(21) Appl. No.: 16/638,330

(22) PCT Filed: Aug. 29, 2017

(86) PCT No.: PCT/TH2017/000066
§ 371 (c)(1),
(2) Date: Feb. 11, 2020

(87) PCT Pub. No.: WO2019/045655
PCT Pub. Date: Mar. 7, 2019

(65) Prior Publication Data
US 2020/0223820 A1    Jul. 16, 2020

(51) Int. Cl.
*C07D 215/44* (2006.01)
*A61K 31/47* (2006.01)
*C07D 401/12* (2006.01)
*A61P 31/18* (2006.01)
*A61P 35/02* (2006.01)

(52) U.S. Cl.
CPC ............ *C07D 401/12* (2013.01); *A61P 31/18* (2018.01); *A61P 35/02* (2018.01)

(58) Field of Classification Search
CPC .. C07D 215/44; C07D 215/22; C07D 471/04; A61K 31/47; A61K 31/4375
USPC ......... 546/160, 157, 122; 514/313, 312, 300
See application file for complete search history.

(56) References Cited

U.S. PATENT DOCUMENTS 7,153,865 B2 * 12/2006 D'Amico ................ A61P 25/04
514/313
8,222,403 B2 * 7/2012 Laskoski ................ B82Y 25/00
524/431

OTHER PUBLICATIONS

Fulton, J.D. et al.: Amoebicidal action and chemical constitution. Proceedings of the Royal Society of London, series B, biological sciences, vol. 137, pp. 339=366, 1950.*

* cited by examiner

*Primary Examiner* — Charanjit Aulakh
(74) *Attorney, Agent, or Firm* — Ladas & Parry LLP

(57) ABSTRACT

Derivatives of quinoline and naphthyridine, methods of making such compounds, and methods of using such compounds for the treatment or prophylaxis of HIV infection and certain cancers.

14 Claims, No Drawings

DERIVATIVES AND COMPOSITION OF QUINOLINE AND NAPHTHYRIDINE

RELATED APPLICATION

This application is an application under 35 U.S.C. 371 of International Application No. PCT/TH2017/000066 filed on 29 Aug. 2017, the entire contents of which are incorporated herein by reference.

FIELD OF INVENTION

This invention relates to the novel derivatives of quinoline and naphthyridine, the methods of making such compounds, and the methods of using such compounds for the treatment or prevention of diseases, especially HIV infection and cancer.

BACKGROUND ART

Non-nucleoside reverse transcriptase inhibitors (NNRTIs) have proven efficacy against human immunodeficiency virus type 1 (HIV-1). First-generation NNRTIs, namely, efavirenz (EFV) and nevirapine (NVP), are common components of first-line and highly active antiretroviral (ARV) therapy for HIV-1 patients. EFV and NVP both exhibit long-term efficacy, generally good tolerability, and low pill burden. However, the clinical use of EFV and NVP can be limited because of their relatively low genetic barrier to resistance, the cross-resistance between them, and some tolerability issues. In this regard, various strategies have been developed to identify next-generation agents with activities against NNRTI-resistant viruses. One of these strategies such as the computational chemistry using molecular docking led to the identification of etravirine (ETR; TMC125) as a diarylpyrimidine NNRTI with activity against a broad spectrum of wild-type and first-generation NNRTI-resistant HIV-1 viruses. The same strategy was used to characterize TMC278 (rilpivirine) as a second NNRTI of the diarylpyrimidine family. Meanwhile, TMC278 is a potential clinical candidate currently under evaluation in treatment-naïve patients (Azijn H, Tirry I, Vingerhoets J, et al., TMC278, A Next-Generation Nonnucleoside Reverse Transcriptase Inhibitor (NNRTI), Active against Wild-Type and NNRTI-Resistant HIV-1, Antimicrobial Agents and Chemotherapy, 2010; 54(2):718-727, doi:10.1128/AAC.00986-09).

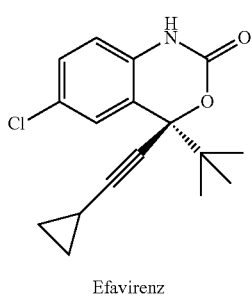

Efavirenz

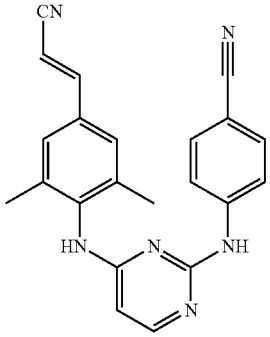

TMC278

Precancerous lesions in HIV-1-infected patients was recently reported to regress after the initiation of highly active antiretroviral therapy. NNRTIs, such as EFVs, might be mediators of the regression, because of their cytotoxicity against tumor cells. In addition, a potential mechanism involved in this effect is the activation of cannabinoid receptors, such as CB1 and CB2, which mediate tumor toxicity. EFV exerts selective cytotoxic effects on several tumor cell lines but not on primary fibroblasts. These cytotoxic effects are associated with CB1 expression. Furthermore, EFV promotes the phosphorylation of the tumor suppressor protein p53, as revealed in previous studies, which reported that EFV is a potential antitumorigenic and cytostatic drug (Hecht M, et al., Cytotoxic effect of efavirenz is selective against cancer cells and associated with the cannabinoid system, AIDS, 2013 Aug. 24; 27(13):2031-40, doi: 10.1097/QAD.0b013e3283625444).

Cancer prevention and therapy in HIV-1-infected patients are expected to play an important role in the future. NNRTIs, particularly EFV and NVP, are cytotoxic against cancer cells in vitro. However, studies on other NNRTIs are few. Thus, the current work tests all clinically used NNRTIs, and their in vitro toxic concentrations are compared with drug levels in patients to predict possible anticancer effects in viva. The in vitro $EC_{50}$ values of the drugs used in BxPC-3 pancreatic cancer cells are 315 µmol/L EFV and 24.4 µmol/L TMC278. Among the NNRTIs, EFV and TMC278 exhibit the highest cytotoxic potential against pancreatic cancer cells at low concentrations. Notably, those studied NNRTIs are toxic against cancer cells over a broad range of toxic concentrations. The toxicity of NNRTIs against cancer cells promotes the idea to use these drugs in HIV-1-infected patients to prevent or even treat cancer (Hecht M, Erber S, Harrer T, et al. Efavirenz Has the Highest Anti-Proliferative Effect of Non-Nucleoside Reverse Transcriptase Inhibitors against Pancreatic Cancer Cells. Menéndez-Arias L, ed. PLoS ONE.2015; 10(6):e0130277.doi:10.1371/journal.pone.0130277).

SUMMARY OF THE INVENTION

In the present invention, novel derivatives of quinoline and naphthyridine that are useful for the treatment of diseases, especially HIV infection and cancer, are introduced.

The compounds of the present invention have the following formula:

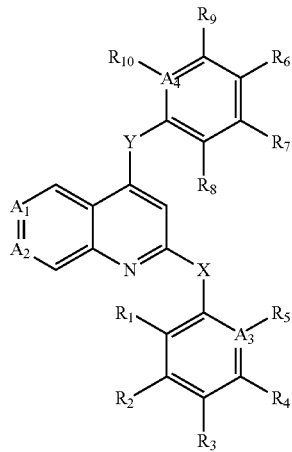

(I)

where

X and Y may be identical or different and represent O, NH, or S;

$R_1$, $R_2$, $R_3$, $R_4$, $R_5$, $R_6$, $R_7$, $R_8$, $R_9$, and $R_{10}$ may be identical or different and represent H, halogen, CN, $NO_2$, $(C_{1-4})$alkyl, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^A$, $C(O)R^A$, $CO_2R^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R^A$ and $R^B$ may be identical or different, and both may represent H, $(C_{1-4})$alkyl, $(C_{1-4})$haloalkyl, or $(C_{2-4})$alkenyl;

$A_1$, $A_2$, $A_3$, and $A_4$ may be identical or different and represent CH or N, but $A_1$ and $A_2$ cannot both be N, and $R_5$ and $R_{10}$ are absent when $A_3$ and $A_4$ are N;

or a pharmaceutically acceptable salt thereof, stereoisomer thereof, or mixture comprising stereoisomers thereof.

Particular compounds of the present invention are those of the formula (I) in which X and Y may be identical or different and represent O, NH, or S;

$R_1$, $R_2$, $R_3$, $R_4$, and $R_5$ may be identical or different and represent H, halogen, CN, $NO_2$, $(C_{1-4})$alkyl, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^B$, $C(O)R^A$, $COR^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R_6$, $R_7$, $R_8$, $R_9$, and $R_{10}$ may be identical or different and represent H, CN, $NO_2$, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^B$, $C(O)R^A$, $CO_2R^A$, CHO, $C_{2-4}$alkenyl substituted with CN, $C_{2-4}$ alkenyl substituted with COOH, $C_{2-4}$ alkenyl substituted with CHO, or $C_{2-4}$ alkenyl substituted with OH;

$R^A$ and $R^B$ may be identical or different and represent H, $(C_{1-4})$alkyl, $(C_{1-4})$haloalkyl or $(C_{2-4})$alkenyl;

$A_1$, $A_2$, $A_3$, and $A_4$ may be identical or different and represent CH or N with the proviso that $A_1$ and $A_2$ cannot both be N. $R_5$ and $R_{10}$ are absent when $A_3$ and $A_4$ are N;

or a pharmaceutically acceptable salt thereof, stereoisomer thereof, or mixture comprising stereoisomers thereof.

Particular compounds of the present invention are those of the formula (I) in which X and Y may be identical or different and represent O, NH, or S;

$R_1$, $R_2$, $R_3$, $R_4$, $R_5$, $R_6$, $R_7$, $R_8$, and $R_9$ may be identical or different and represent H, halogen, CN, $NO_2$, $(C_{1-4})$alkyl, $(C_{1-4})$haloalkyl, $(C_{2-4})$alkenyl, OH, $O(C_{1-4}$alkyl, $O(C_{1-4})$haloalkyl, $N(R^A)R^B$, $C(O)N(R^A)R^B$, $C(O)R^A$, $C(O)_2R^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R^A$ and $R^B$ may be identical or different and represent H, $(C_{1-4})$alkyl, $(C_{1-4})$haloalkyl or $(C_{2-4})$alkenyl;

$A_1$, $A_2$, and $A_3$ may be identical or different and represent CH or N with the proviso that $A_1$ and $A_2$ cannot both be N and that $R_5$ is absent when $A_3$ is N;

$A_4$ represents N;

or a pharmaceutically acceptable salt thereof, stereoisomer thereof, or mixture comprising stereoisomers thereof.

Particular compounds of the present invention also include those of the formula (I) in which X and Y may be identical or different and represent O, NH, or S with the proviso that X and Y cannot both be NH or X and Y cannot both be O;

$R_1$, $R_2$, $R_3$, $R_4$, $R_5$, $R_6$, $R_7$, $R_8$, $R_9$, and $R_{10}$ may be identical or different and represent H, halogen, CN, $NO_2$, $(C_{1-4})$alkyl, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^B$, $C(O)R^A$, $CO_2R^A$, CHO, $C_{2-4}$ alkenyl substituted with CN, $C_{2-4}$ alkenyl substituted with COOH, $C_{1-4}$ alkenyl substituted with CHO, or $C_{2-4}$ alkenyl substituted with OH;

$R^A$ and $R^B$ may be identical or different, and both may represent H, $(C_{1-4})$alkyl, $(C_{1-4})$haloalkyl, or $(C_{2-4})$alkenyl;

$A_1$, $A_2$, $A_3$, and $A_4$ may be identical or different and represent CH or N with the proviso that $A_1$ and $A_2$ cannot both be N and that $R_5$ and $R_{10}$ are absent when $A_3$ and $A_4$ are N;

or a pharmaceutically acceptable salt thereof, stereoisomer thereof, or mixture comprising stereoisomers thereof.

Particular compounds of the present invention are those of the formula (I) in which X and Y may be identical or different and represent O, NH, or S;

$R_1$, $R_2$, $R_4$, $R_5$, $R_6$, $R_7$, $R_8$, $R_9$, and $R_{10}$ may be identical or different and represent H, halogen, CN, $NO_2$, $(C_{1-4})$alkyl, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^B$, $C(O)R^A$, $CO_2R^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R_3$ is CN;

$R^A$ and $R^B$ may be identical or different and represent H, $(C_{1-4})$alkyl, $(C_{1-4})$haloalkyl, or $(C_{2-4})$alkenyl;

$A_1$, $A_2$, $A_3$, and $A_4$ may be identical or different and represent CH or N with the proviso that $A_1$ and $A_2$ cannot both be N and that $R_5$ and $R_{10}$ are absent when both $A_3$ and $A_4$ are N;

or a pharmaceutically acceptable salt thereof, stereoisomer thereof, or mixture comprising stereoisomers thereof.

Particular compounds of the present invention also include those of the formula (I) in which X and Y may be identical or different and represent O, NH, or S;

$R_1$, $R_2$, $R_4$, $R_5$, $R_6$, $R_7$, $R_8$, $R_9$, and $R_{10}$ may be identical or different and represent H, halogen, CN, $NO_2$, $(C_{1-4})$alkyl, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^B$, $C(O)R^A$, $CO_2R^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R_3$ is CHO;

$R^A$ and $R^B$ may be identical or different and represent H, $(C_{1-4})$alkyl, $(C_{1-4})$haloalkyl, or $(C_{2-4})$alkenyl;

$A_1$, $A_2$, $A_3$, and $A_4$ may be identical or different and represent CH or N with the proviso that $A_1$ and $A_2$ cannot both be N and $R_5$ and that $R_{10}$ is absent when $A_3$ and $A_4$ are N;

or a pharmaceutically acceptable salt thereof, stereoisomer thereof, or mixture comprising stereoisomers thereof.

Most particular compounds of the invention are those exemplified herein.

In one aspect, the present invention provides a pharmaceutical composition comprising a therapeutically effective amount of a compound according to the invention or a pharmaceutically acceptable salt thereof and one or more pharmaceutically acceptable carriers or excipients or diluents In one aspect, the present invention provides the compound according to the present invention for used in therapy.

In one aspect, the present invention provides the compound according to the present invention for use in the treatment or prevention of HIV infection.

In one aspect, the present invention provides the compound according to the present invention for use in combination with other antiretroviral agent(s) for the treatment or prevention of HIV infection.

In one aspect, the present invention provides the compound according to the present invention for use in the treatment or prevention of cancer.

In one aspect, the present invention provides the compound according to the present invention for use in combination with radiation and/or other chemotherapeutic agent(s) for the treatment or prevention of cancer.

In one aspect, the present invention is directed to use of a compound according to the present invention for use in manufacture of a medicament for treating or preventing HIV infection.

In one aspect, the present invention is directed to use of a compound according to the present invention in manufacture of a medicament for treating or preventing cancer.

In one aspect, the present invention is directed to use of a compound according to the present invention and other antiretroviral agent(s) in manufacture of a medicament for treating or preventing HIV infection.

In one aspect, the present invention is directed to use of a compound according to the present invention and other chemotherapeutic agent(s) in manufacture of a medicament for treating cancer.

In one aspect, the present invention is directed to a combination of a compound according to the present invention and other antiretroviral agent(s) for use in manufacture of a medicament for treating or preventing HIV infection.

In one aspect, the present invention is directed to a combination of a compound according to the present invention and other chemotherapeutic agent(s) for use in manufacture of a medicament for treating or preventing cancer.

In one aspect, the present invention provides a method for the treatment or prevention of HIV infection in a patient, comprising administering to a patient an HIV inhibitory dose of a compound according to the present invention or a pharmaceutically acceptable salt thereof or a pharmaceutical composition comprising a compound of the present invention.

In one aspect, the present invention provides a method for the treatment or prevention of cancer in a patient, comprising administering to a patient a cancer inhibitory dose of a compound according to the present invention or a pharmaceutically acceptable salt thereof or a pharmaceutical composition comprising a compound of the present invention.

In one aspect, the present invention provides a method for the treatment or prevention of HIV infection comprises administering to a patient an HIV inhibitory dose of a compound according to the present invention or a pharmaceutically acceptable salt thereof or a pharmaceutical composition comprising a compound of the present invention in combination with other antiretroviral agent(s).

In one aspect, the present invention provides a method for the treatment or prevention of cancer comprises administering to a patient a cancer inhibitory dose of a compound according to the present invention or a pharmaceutically acceptable salt thereof or a pharmaceutical composition comprising a compound of the present invention in combination with radiation and/or other chemotherapeutic agent(s).

DETAILED DESCRIPTION

Viruses resistant to first-generation NVP and EFV carry one or several mutations in their reverse transcriptase (RT) genes. These mutations immediately confer high-level resistance, as well as cross-resistance, to the two drugs. Such mutations have been detected to be close to the binding site of NNRTIs and connection domain of HIV RT. They can lead to a loss of drug affinity without affecting viral fitness (Ghosn J, Chaix M L and Delaugerre C. Aids Rev. 2009 11(3): 165-173). NVP, EFV, and TMC278 bind to the same binding site at different efficiencies in the inhibition of HIV-1 RT. NVP has lower $IC_{50}$ than EFV and TMC278. No significant difference is observed in the $IC_{50}$ values of EFV and TMC278.

After comparing their efficiencies in inhibiting HIV-1 RT, TMC278 is found to be more effective than EFV because the former has more structural flexibility than the latter in the formation of complexes in the binding site. Additionally, EFV shows decreased HIV-1 RT mutations (Domaoal R A and Demeter L M. Int. J. Biochem. Cell. Biol. 2004 36(9): 1735-1751).

The inventor has created a new structure of NNRTIs on the basis of the analyzed molecular characteristics of the first- and second-generation NNRTIs NVP, EFV, and TMC278.

The novel compounds of the present invention are created through hybrid pharmacophore approach based on the structure of EFV and TMC278. In the docking model in which the lower-energy conformations of EFV and TMC278 templates are overlaid within the NNRTI binding sites, most fragments in the EFV and TMC278 structures can superpose effectively.

Given the superimposition between EFV and TMC278, the C=O group of EFV overlaps with the TMC278 core structure, while the side chain of EFV overlays with that of TMC278. Computational chemistry using a molecular docking procedure is applied to discover alternatives or potential HIV-1 RT inhibitors. The novel compounds of the present invention can be developed into medicines HIV and cancer treatments. Both the side chains of TMC278 are incorporated into the structure of the novel compound. The estimated free energy of the binding obtained from the AutoDock procedure is determined to investigate potential NNRTIs. The estimated free energy of the binding of quinoline, 1,6-naphthyridine, and 1,7-naphtylridine obtained from the AutoDock procedure is lower than that of TMC278. Substituent groups at positions 2 and 4 of quinoline, 1,6-naphthyridine, and 1,7-naphtylridine are then assigned to create novel compounds in the docking procedure.

In the present invention, a series of EFV-TMC278 hybrids, characterized by 2,4-substituted quinoline (1), 2,4-substituted 1,6-naphthyridine (2), and 2,4-substituted 1,7-naphtyridine (3) are synthesized. These novel compounds show an excellent biological activity against HIV infection and cancer proliferation.

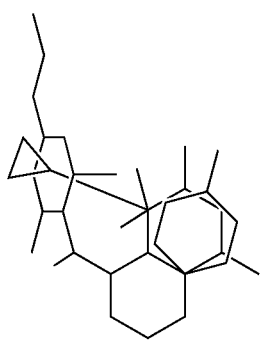

EFV-TMC278 hybrid

Examples of compounds based on the invention are provided in Tables 1-24. These examples are provided to enable those skilled in the art to clearly understand and practice the present invention. They should not be considered as a limitation in the scope of the invention but merely as an illustrative and representation.

The compounds in the following tables are depicted with generalized substituents; however, the nature of the R groups varies to afford various compounds considered in this invention.

TABLE 1

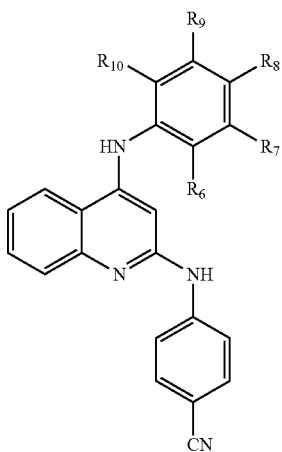

| Entry | $R_6$ | $R_7$ | $R_8$ | $R_9$ | $R_{10}$ | BE | ABE | NOC |
|---|---|---|---|---|---|---|---|---|
| 1-01 | H | H | CHO | H | H | −12.16 | −11.95 | 92 |
| 1-02 | $CH_3$ | H | CHO | H | $CH_3$ | −13.05 | −12.87 | 120 |
| 1-03 | H | H | COOH | H | H | −11.65 | −11.33 | 65 |

TABLE 1-continued

| 1-04 | $CH_3$ | H | COOH | H | $CH_3$ | −12.56 | −12.28 | 101 |
|---|---|---|---|---|---|---|---|---|
| 1-05 | H | H | $COCH_3$ | H | H | −12.83 | −12.44 | 68 |
| 1-06 | $CH_3$ | H | $COCH_3$ | H | $CH_3$ | −13.77 | −13.45 | 99 |
| 1-07 | H | H | $COOCH_3$ | H | H | −12.55 | −11.95 | 44 |
| 1-08 | $CH_3$ | H | $COOCH_3$ | H | $CH_3$ | −13.50 | −12.83 | 53 |
| 1-09 | H | H | CN | H | H | −12.59 | −12.24 | 135 |
| 1-10 | $CH_3$ | H | CN | H | $CH_3$ | −13.48 | −13.28 | 123 |
| 1-11 | H | F | CN | H | H | −12.83 | −12.27 | 86 |
| 1-12 | H | F | CN | F | H | −12.79 | −12.08 | 71 |
| 1-13 | H | $CH_3$ | H | $CH_3$ | H | −11.97 | −11.23 | 18 |
| 1-14 | Br | H | CHO | H | Br | −13.97 | −13.67 | 117 |
| 1-15 | H | H | OH | H | H | −11.57 | −11.12 | 12 |
| 1-16 | H | OH | H | OH | H | −10.98 | −10.48 | 32 |

TABLE 2

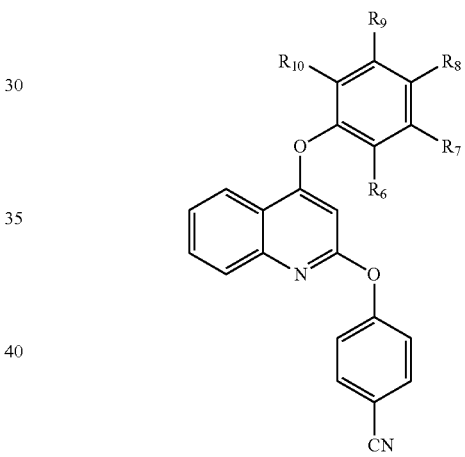

| Entry | $R_6$ | $R_7$ | $R_8$ | $R_9$ | $R_{10}$ | BE | ABE | NOC |
|---|---|---|---|---|---|---|---|---|
| 2-01 | H | H | CHO | H | H | −11.83 | −11.63 | 73 |
| 2-02 | $CH_3$ | H | CHO | H | $CH_3$ | −12.93 | −12.7 | 122 |
| 2-03 | H | H | COOH | H | H | −11.33 | −11.07 | 57 |
| 2-04 | $CH_3$ | H | COOH | H | $CH_3$ | −12.47 | −12.12 | 104 |
| 2-05 | H | H | $COCH_3$ | H | H | −12.56 | −12.2 | 64 |
| 2-06 | $CH_3$ | H | $COCH_3$ | H | $CH_3$ | −13.63 | −13.23 | 110 |
| 2-07 | H | H | $COOCH_3$ | H | H | −12.22 | −11.68 | 55 |
| 2-08 | $CH_3$ | H | $COOCH_3$ | H | $CH_3$ | −13.34 | −12.64 | 76 |
| 2-09 | H | H | CN | H | H | −12.29 | −11.97 | 135 |
| 2-10 | $CH_3$ | H | CN | H | $CH_3$ | −13.38 | −13.18 | 131 |
| 2-11 | H | F | CN | H | H | −12.65 | −12.24 | 103 |
| 2-12 | H | F | CN | F | H | −12.77 | −12.19 | 72 |
| 2-13 | H | $CH_3$ | H | $CH_3$ | H | −12.05 | −11.46 | 29 |
| 2-14 | Br | H | CHO | H | Br | −13.77 | −13.48 | 125 |
| 2-15 | H | H | OH | H | H | −11.48 | −11.02 | 27 |
| 2-16 | H | OH | H | OH | H | −11.45 | −11.16 | 5 |

TABLE 3

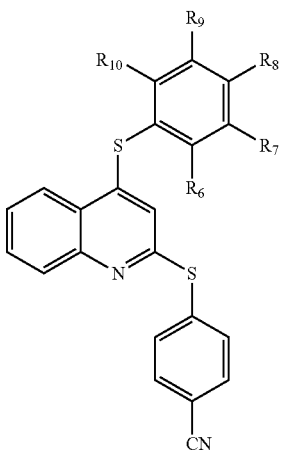

| Entry | $R_6$ | $R_7$ | $R_8$ | $R_9$ | $R_{10}$ | BE | ABE | NOC |
|---|---|---|---|---|---|---|---|---|
| 3-01 | H | H | CHO | H | H | −11.90 | −11.67 | 76 |
| 3-02 | CH$_3$ | H | CHO | H | CH$_3$ | −12.22 | −11.75 | 21 |
| 3-03 | H | H | COOH | H | H | −11.38 | −11.03 | 49 |
| 3-04 | CH$_3$ | H | COOH | H | CH$_3$ | −11.73 | −10.76 | 10 |
| 3-05 | H | H | COCH$_3$ | H | H | −12.45 | −12.06 | 64 |
| 3-06 | CH$_3$ | H | COCH$_3$ | H | CH$_3$ | −12.50 | −11.53 | 8 |
| 3-07 | H | H | COOCH$_3$ | H | H | −12.27 | −11.68 | 38 |
| 3-08 | CH$_3$ | H | COOCH$_3$ | H | CH$_3$ | −12.19 | −11.49 | 7 |
| 3-09 | H | H | CN | H | H | −12.13 | −11.74 | 110 |
| 3-10 | CH$_3$ | H | CN | H | CH$_3$ | −12.49 | −12.10 | 7 |
| 3-11 | H | F | CN | H | H | −12.44 | −11.98 | 86 |
| 3-12 | H | F | CN | F | H | −11.93 | −11.44 | 11 |
| 3-13 | H | CH$_3$ | H | CH$_3$ | H | −12.51 | −12.05 | 85 |
| 3-14 | Br | H | CHO | H | Br | −12.21 | −11.74 | 39 |
| 3-15 | H | H | OH | H | H | −11.55 | −11.08 | 16 |
| 3-16 | H | OH | H | OH | H | −11.47 | −10.77 | 30 |

TABLE 4

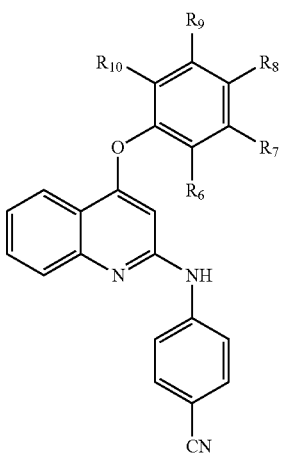

| Entry | $R_6$ | $R_7$ | $R_8$ | $R_9$ | $R_{10}$ | BE | ABE | NOC |
|---|---|---|---|---|---|---|---|---|
| 4-01 | H | H | CHO | H | H | −12.11 | −11.96 | 97 |
| 4-02 | CH$_3$ | H | CHO | H | CH$_3$ | −13.21 | −12.99 | 118 |
| 4-03 | H | H | COOH | H | H | −11.61 | −11.40 | 87 |
| 4-04 | CH$_3$ | H | COOH | H | CH$_3$ | −12.74 | −12.45 | 111 |
| 4-05 | H | H | COCH$_3$ | H | H | −12.81 | −12.47 | 74 |
| 4-06 | CH$_3$ | H | COCH$_3$ | H | CH$_3$ | −13.90 | −13.48 | 100 |
| 4-07 | H | H | COOCH$_3$ | H | H | −12.55 | −12.10 | 61 |
| 4-08 | CH$_3$ | H | COOCH$_3$ | H | CH$_3$ | −13.64 | −12.99 | 78 |
| 4-09 | H | H | CN | H | H | −12.55 | −12.38 | 126 |
| 4-10 | CH$_3$ | H | CN | H | CH$_3$ | −13.65 | −13.48 | 131 |
| 4-11 | H | F | CN | H | H | −12.90 | −12.59 | 87 |
| 4-12 | H | F | CN | F | H | −12.93 | −12.46 | 50 |
| 4-13 | H | CH$_3$ | H | CH$_3$ | H | −12.19 | −11.76 | 42 |
| 4-14 | Br | H | CHO | H | Br | −14.05 | −13.81 | 119 |
| 4-15 | H | H | OH | H | H | −11.30 | −11.18 | 83 |
| 4-16 | H | OH | H | OH | H | −11.26 | −10.90 | 42 |

TABLE 5

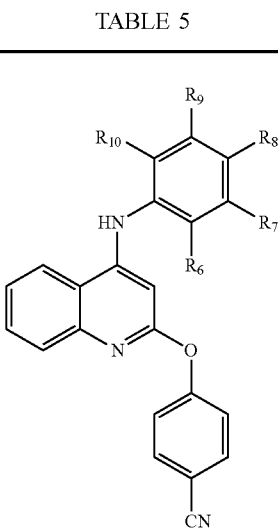

| Entry | $R_6$ | $R_7$ | $R_8$ | $R_9$ | $R_{10}$ | BE | ABE | NOC |
|---|---|---|---|---|---|---|---|---|
| 5-01 | H | H | CHO | H | H | −11.87 | −11.68 | 55 |
| 5-02 | CH$_3$ | H | CHO | H | CH$_3$ | −12.76 | −12.54 | 117 |
| 5-03 | H | H | COOH | H | H | −11.41 | −10.93 | 50 |
| 5-04 | CH$_3$ | H | COOH | H | CH$_3$ | −12.26 | −12.03 | 99 |
| 5-05 | H | H | COCH$_3$ | H | H | −12.58 | −12.22 | 55 |
| 5-06 | CH$_3$ | H | COCH$_3$ | H | CH$_3$ | −13.45 | −13.04 | 93 |
| 5-07 | H | H | COOCH$_3$ | H | H | −12.29 | −11.61 | 33 |
| 5-08 | CH$_3$ | H | COOCH$_3$ | H | CH$_3$ | −13.23 | −12.53 | 72 |
| 5-09 | H | H | CN | H | H | −12.30 | −12.00 | 133 |
| 5-10 | CH$_3$ | H | CN | H | CH$_3$ | −13.22 | −13.03 | 127 |
| 5-11 | H | F | CN | H | H | −12.63 | −12.16 | 60 |
| 5-12 | H | F | CN | F | H | −12.61 | −12.06 | 22 |
| 5-13 | H | CH$_3$ | H | CH$_3$ | H | −11.93 | −11.51 | 41 |
| 5-14 | Br | H | CHO | H | Br | −13.65 | −13.37 | 124 |
| 5-15 | H | H | OH | H | H | −11.61 | −11.23 | 21 |
| 5-16 | H | OH | H | OH | H | −11.29 | −10.80 | 13 |

TABLE 6

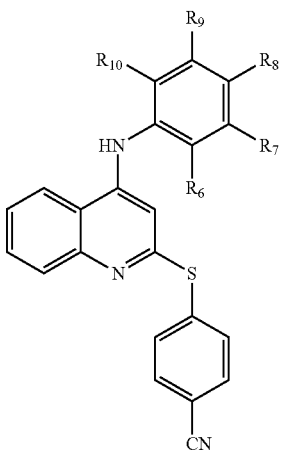

| Entry | R6 | R7 | R8 | R9 | R10 | BE | ABE | NOC |
|---|---|---|---|---|---|---|---|---|
| 6-01 | H | H | CHO | H | H | −11.63 | −11.32 | 125 |
| 6-02 | CH3 | H | CHO | H | CH3 | −12.22 | −11.80 | 74 |
| 6-03 | H | H | COOH | H | H | −11.14 | −10.61 | 96 |
| 6-04 | CH3 | H | COOH | H | CH3 | −11.66 | −11.26 | 42 |
| 6-05 | H | H | COCH3 | H | H | −12.27 | −11.65 | 101 |
| 6-06 | CH3 | H | COCH3 | H | CH3 | −12.62 | −11.95 | 36 |
| 6-07 | H | H | COOCH3 | H | H | −12.13 | −11.24 | 71 |
| 6-08 | CH3 | H | COOCH3 | H | CH3 | −12.43 | −12.09 | 22 |
| 6-09 | H | H | CN | H | H | −12.03 | −11.74 | 125 |
| 6-10 | CH3 | H | CN | H | CH3 | −12.73 | −12.34 | 95 |
| 6-11 | H | F | CN | H | H | −12.54 | −12.01 | 76 |
| 6-12 | H | F | CN | F | H | −12.15 | −11.35 | 70 |
| 6-13 | H | CH3 | H | CH3 | H | −12.01 | −11.04 | 52 |
| 6-14 | Br | H | CHO | H | Br | −12.22 | −11.91 | 104 |
| 6-15 | H | H | OH | H | H | −11.64 | −11.24 | 10 |
| 6-16 | H | OH | H | OH | H | −11.17 | −10.96 | 4 |

TABLE 7

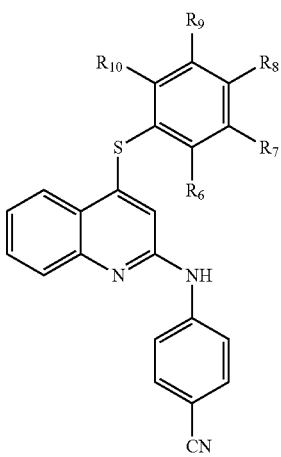

| Entry | R6 | R7 | R8 | R9 | R10 | BE | ABE | NOC |
|---|---|---|---|---|---|---|---|---|
| 7-01 | H | H | CHO | H | H | −11.78 | −11.45 | 110 |
| 7-02 | CH3 | H | CHO | H | CH3 | −12.81 | −12.40 | 117 |
| 7-03 | H | H | COOH | H | H | −11.17 | −10.84 | 17 |
| 7-04 | CH3 | H | COOH | H | CH3 | −12.13 | −11.52 | 100 |
| 7-05 | H | H | COCH3 | H | H | −12.31 | −11.72 | 72 |
| 7-06 | CH3 | H | COCH3 | H | CH3 | −13.35 | −12.68 | 106 |
| 7-07 | H | H | COOCH3 | H | H | −12.05 | −11.40 | 64 |
| 7-08 | CH3 | H | COOCH3 | H | CH3 | −13.16 | −12.40 | 83 |
| 7-09 | H | H | CN | H | H | −12.11 | −11.81 | 96 |
| 7-10 | CH3 | H | CN | H | CH3 | −13.06 | −12.65 | 127 |
| 7-11 | H | F | CN | H | H | −12.56 | −12.08 | 94 |
| 7-12 | H | F | CN | F | H | −12.69 | −12.09 | 104 |
| 7-13 | H | CH3 | H | CH3 | H | −12.59 | −12.00 | 79 |
| 7-14 | Br | H | CHO | H | Br | −13.77 | −13.30 | 119 |
| 7-15 | H | H | OH | H | H | −11.56 | −11.05 | 29 |
| 7-16 | H | OH | H | OH | H | −11.32 | −10.97 | 11 |

TABLE 8

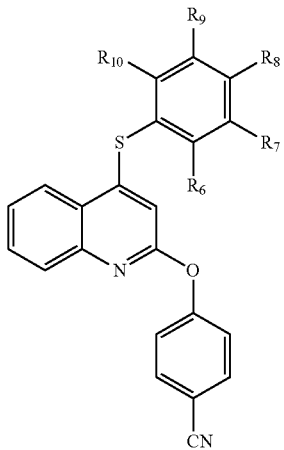

| Entry | R6 | R7 | R8 | R9 | R10 | BE | ABE | NOC |
|---|---|---|---|---|---|---|---|---|
| 8-01 | H | H | CHO | H | H | −11.69 | −11.41 | 40 |
| 8-02 | CH3 | H | CHO | H | CH3 | −12.56 | −12.09 | 116 |
| 8-03 | H | H | COOH | H | H | −11.35 | −10.96 | 22 |
| 8-04 | CH3 | H | COOH | H | CH3 | −11.91 | −11.28 | 97 |
| 8-05 | H | H | COCH3 | H | H | −12.04 | −11.59 | 18 |
| 8-06 | CH3 | H | COCH3 | H | CH3 | −13.12 | −12.46 | 92 |
| 8-07 | H | H | COOCH3 | H | H | −11.84 | −11.11 | 47 |
| 8-08 | CH3 | H | COOCH3 | H | CH3 | −12.86 | −12.01 | 86 |
| 8-09 | H | H | CN | H | H | −11.98 | −11.66 | 111 |
| 8-10 | CH3 | H | CN | H | CH3 | −12.90 | −12.53 | 115 |
| 8-11 | H | F | CN | H | H | −12.25 | −11.77 | 73 |
| 8-12 | H | F | CN | F | H | −12.21 | −11.69 | 93 |
| 8-13 | H | CH3 | H | CH3 | H | −12.35 | −11.75 | 72 |
| 8-14 | Br | H | CHO | H | Br | −13.51 | −13.06 | 106 |
| 8-15 | H | H | OH | H | H | −11.78 | −11.43 | 34 |
| 8-16 | H | OH | H | OH | H | −11.60 | −11.19 | 12 |

TABLE 9

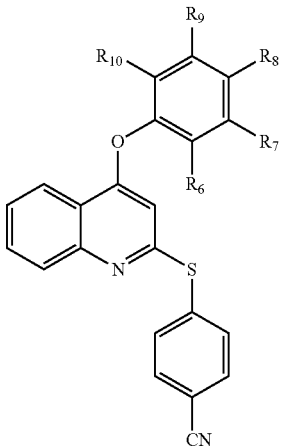

| Entry | $R_6$ | $R_7$ | $R_8$ | $R_9$ | $R_{10}$ | BE | ABE | NOC |
|---|---|---|---|---|---|---|---|---|
| 9-01 | H | H | CHO | H | H | −11.72 | −11.53 | 123 |
| 9-02 | $CH_3$ | H | CHO | H | $CH_3$ | −12.49 | −12.11 | 136 |
| 9-03 | H | H | COOH | H | H | −11.24 | −10.74 | 103 |
| 9-04 | $CH_3$ | H | COOH | H | $CH_3$ | −11.91 | −11.42 | 115 |
| 9-05 | H | H | $COCH_3$ | H | H | −12.38 | −11.93 | 102 |
| 9-06 | $CH_3$ | H | $COCH_3$ | H | $CH_3$ | −13.08 | −12.51 | 113 |
| 9-07 | H | H | $COOCH_3$ | H | H | −12.21 | −11.48 | 68 |
| 9-08 | $CH_3$ | H | $COOCH_3$ | H | $CH_3$ | −12.92 | −12.52 | 33 |
| 9-09 | H | H | CN | H | H | −12.09 | −11.89 | 124 |
| 9-10 | $CH_3$ | H | CN | H | $CH_3$ | −12.93 | −12.62 | 137 |
| 9-11 | H | F | CN | H | H | −12.57 | −12.18 | 116 |
| 9-12 | H | F | CN | F | H | −12.71 | −12.26 | 100 |
| 9-13 | H | $CH_3$ | H | $CH_3$ | H | −12.16 | −11.46 | 66 |
| 9-14 | Br | H | CHO | H | Br | −13.36 | −12.99 | 139 |
| 9-15 | H | H | OH | H | H | −11.42 | −11.11 | 30 |
| 9-16 | H | OH | H | OH | H | −11.29 | −10.61 | 30 |

TABLE 10

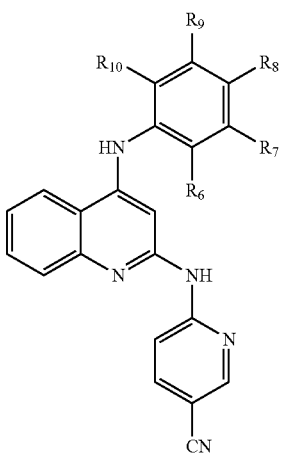

| Entry | $R_6$ | $R_7$ | $R_8$ | $R_9$ | $R_{10}$ | BE | ABE | NOC |
|---|---|---|---|---|---|---|---|---|
| 10-01 | H | H | CHO | H | H | −11.75 | −11.46 | 75 |
| 10-02 | $CH_3$ | H | CHO | H | $CH_3$ | −12.64 | −12.43 | 109 |
| 10-03 | H | H | COOH | H | H | −11.28 | −10.85 | 59 |
| 10-04 | $CH_3$ | H | COOH | H | $CH_3$ | −12.14 | −11.83 | 93 |
| 10-05 | H | H | $COCH_3$ | H | H | −12.45 | −11.99 | 58 |
| 10-06 | $CH_3$ | H | $COCH_3$ | H | $CH_3$ | −13.33 | −12.99 | 85 |
| 10-07 | H | H | $COOCH_3$ | H | H | −12.13 | −11.57 | 35 |
| 10-08 | $CH_3$ | H | $COOCH_3$ | H | $CH_3$ | −13.08 | −12.55 | 55 |
| 10-09 | H | H | CN | H | H | −12.18 | −11.81 | 132 |
| 10-10 | $CH_3$ | H | CN | H | $CH_3$ | −13.08 | −12.89 | 126 |
| 10-11 | H | F | CN | H | H | −12.45 | −11.84 | 70 |
| 10-12 | H | F | CN | F | H | −12.46 | −11.67 | 49 |
| 10-13 | H | $CH_3$ | H | $CH_3$ | H | −11.69 | −11.13 | 21 |
| 10-14 | Br | H | CHO | H | Br | −13.55 | −13.29 | 103 |
| 10-15 | H | H | OH | H | H | −11.13 | −10.90 | 12 |
| 10-16 | H | OH | H | OH | H | −10.65 | −10.37 | 21 |

TABLE 11

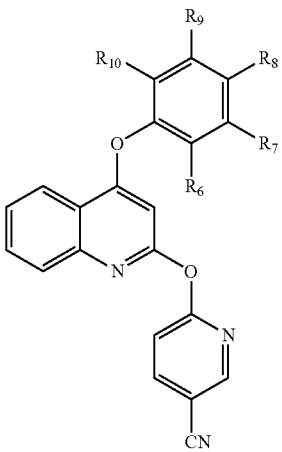

| Entry | $R_6$ | $R_7$ | $R_8$ | $R_9$ | $R_{10}$ | BE | ABE | NOC |
|---|---|---|---|---|---|---|---|---|
| 11-01 | H | H | CHO | H | H | −11.52 | −11.25 | 78 |
| 11-02 | $CH_3$ | H | CHO | H | $CH_3$ | −12.60 | −12.30 | 122 |
| 11-03 | H | H | COOH | H | H | −11.01 | −10.72 | 58 |
| 11-04 | $CH_3$ | H | COOH | H | $CH_3$ | −12.11 | −11.75 | 101 |
| 11-05 | H | H | $COCH_3$ | H | H | −12.20 | −11.79 | 55 |
| 11-06 | $CH_3$ | H | $COCH_3$ | H | $CH_3$ | −13.31 | −12.84 | 101 |
| 11-07 | H | H | $COOCH_3$ | H | H | −11.95 | −11.28 | 46 |
| 11-08 | $CH_3$ | H | $COOCH_3$ | H | $CH_3$ | −13.03 | −12.34 | 85 |
| 11-09 | H | H | CN | H | H | −11.95 | −11.62 | 127 |
| 11-10 | $CH_3$ | H | CN | H | $CH_3$ | −13.05 | −12.78 | 130 |
| 11-11 | H | F | CN | H | H | −12.32 | −11.84 | 109 |
| 11-12 | H | F | CN | F | H | −12.43 | −11.91 | 58 |
| 11-13 | H | $CH_3$ | H | $CH_3$ | H | −11.73 | −11.15 | 34 |
| 11-14 | Br | H | CHO | H | Br | −13.43 | −13.08 | 123 |
| 11-15 | H | H | OH | H | H | −11.18 | −10.73 | 25 |
| 11-16 | H | OH | H | OH | H | −11.11 | −10.65 | 19 |

TABLE 12

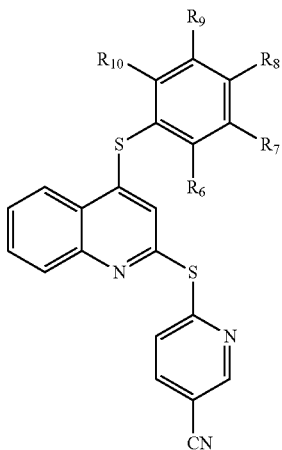

| Entry | $R_6$ | $R_7$ | $R_8$ | $R_9$ | $R_{10}$ | BE | ABE | NOC |
|---|---|---|---|---|---|---|---|---|
| 12-01 | H | H | CHO | H | H | −11.44 | −10.99 | 81 |
| 12-02 | $CH_3$ | H | CHO | H | $CH_3$ | −11.92 | −11.30 | 10 |
| 12-03 | H | H | COOH | H | H | −10.91 | −10.39 | 43 |
| 12-04 | $CH_3$ | H | COOH | H | $CH_3$ | −11.79 | −10.78 | 15 |
| 12-05 | H | H | $COCH_3$ | H | H | −12.08 | −11.16 | 61 |
| 12-06 | $CH_3$ | H | $COCH_3$ | H | $CH_3$ | −11.97 | −11.01 | 33 |
| 12-07 | H | H | $COOCH_3$ | H | H | −11.83 | −11.06 | 36 |
| 12-08 | $CH_3$ | H | $COOCH_3$ | H | $CH_3$ | −12.21 | −10.79 | 9 |
| 12-09 | H | H | CN | H | H | −11.78 | −11.31 | 103 |
| 12-10 | $CH_3$ | H | CN | H | $CH_3$ | −12.26 | −11.32 | 18 |
| 12-11 | H | F | CN | H | H | −12.09 | −11.49 | 66 |
| 12-12 | H | F | CN | F | H | −11.68 | −11.41 | 11 |
| 12-13 | H | $CH_3$ | H | $CH_3$ | H | −12.38 | −11.77 | 81 |
| 12-14 | Br | H | CHO | H | Br | −12.29 | −11.52 | 21 |
| 12-15 | H | H | OH | H | H | −11.18 | −10.75 | 28 |
| 12-16 | H | OH | H | OH | H | −11.58 | −10.80 | 31 |

TABLE 13

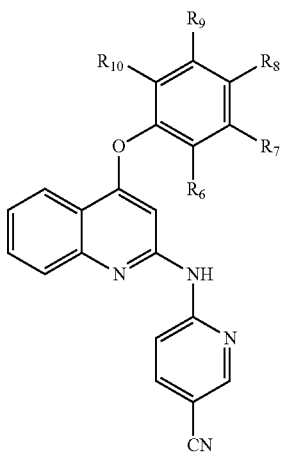

| Entry | $R_6$ | $R_7$ | $R_8$ | $R_9$ | $R_{10}$ | BE | ABE | NOC |
|---|---|---|---|---|---|---|---|---|
| 13-01 | H | H | CHO | H | H | −11.73 | −11.44 | 102 |
| 13-02 | $CH_3$ | H | CHO | H | $CH_3$ | −12.82 | −12.56 | 125 |
| 13-03 | H | H | COOH | H | H | −11.23 | −10.89 | 79 |
| 13-04 | $CH_3$ | H | COOH | H | $CH_3$ | −12.34 | −12.01 | 115 |
| 13-05 | H | H | $COCH_3$ | H | H | −12.41 | −12.06 | 80 |
| 13-06 | $CH_3$ | H | $COCH_3$ | H | $CH_3$ | −13.47 | −13.09 | 105 |
| 13-07 | H | H | $COOCH_3$ | H | H | −12.17 | −11.67 | 49 |
| 13-08 | $CH_3$ | H | $COOCH_3$ | H | $CH_3$ | −13.25 | −12.62 | 79 |
| 13-09 | H | H | CN | H | H | −12.16 | −11.93 | 116 |
| 13-10 | $CH_3$ | H | CN | H | $CH_3$ | −13.26 | −13.01 | 125 |
| 13-11 | H | F | CN | H | H | −12.51 | −12.18 | 88 |
| 13-12 | H | F | CN | F | H | −12.57 | −12.20 | 43 |
| 13-13 | H | $CH_3$ | H | $CH_3$ | H | −11.87 | −11.31 | 50 |
| 13-14 | Br | H | CHO | H | Br | −13.67 | −13.39 | 100 |
| 13-15 | H | H | OH | H | H | −10.98 | −10.63 | 28 |
| 13-16 | H | OH | H | OH | H | −11.00 | −10.46 | 36 |

TABLE 14

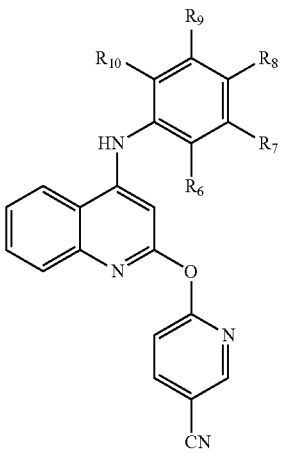

| Entry | $R_6$ | $R_7$ | $R_8$ | $R_9$ | $R_{10}$ | BE | ABE | NOC |
|---|---|---|---|---|---|---|---|---|
| 14-01 | H | H | CHO | H | H | −11.53 | −11.15 | 59 |
| 14-02 | $CH_3$ | H | CHO | H | $CH_3$ | −12.39 | −12.18 | 119 |
| 14-03 | H | H | COOH | H | H | −11.06 | −10.59 | 53 |
| 14-04 | $CH_3$ | H | COOH | H | $CH_3$ | −11.91 | −11.60 | 100 |
| 14-05 | H | H | $COCH_3$ | H | H | −12.16 | −11.76 | 55 |
| 14-06 | $CH_3$ | H | $COCH_3$ | H | $CH_3$ | −13.13 | −12.65 | 93 |
| 14-07 | H | H | $COOCH_3$ | H | H | −11.85 | −11.27 | 33 |
| 14-08 | $CH_3$ | H | $COOCH_3$ | H | $CH_3$ | −12.87 | −12.17 | 53 |
| 14-09 | H | H | CN | H | H | −11.97 | −11.68 | 65 |
| 14-10 | $CH_3$ | H | CN | H | $CH_3$ | −12.87 | −12.64 | 126 |
| 14-11 | H | F | CN | H | H | −12.27 | −11.80 | 35 |
| 14-12 | H | F | CN | F | H | −12.20 | −11.54 | 25 |
| 14-13 | H | $CH_3$ | H | $CH_3$ | H | −11.52 | −11.21 | 25 |
| 14-14 | Br | H | CHO | H | Br | −13.30 | −12.96 | 117 |
| 14-15 | H | H | OH | H | H | −11.28 | −11.28 | 1 |
| 14-16 | H | OH | H | OH | H | −10.86 | −10.68 | 10 |

TABLE 15

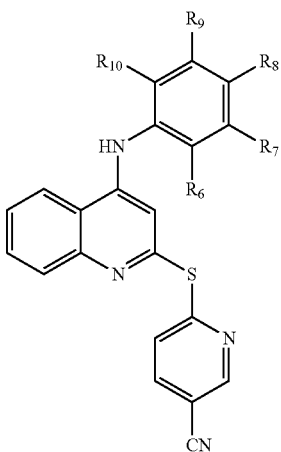

| Entry | R6 | R7 | R8 | R9 | R10 | BE | ABE | NOC |
|---|---|---|---|---|---|---|---|---|
| 15-01 | H | H | CHO | H | H | −11.75 | −11.46 | 75 |
| 15-02 | CH3 | H | CHO | H | CH3 | −12.64 | −12.43 | 109 |
| 15-03 | H | H | COOH | H | H | −11.28 | −10.85 | 59 |
| 15-04 | CH3 | H | COOH | H | CH3 | −12.14 | −11.83 | 93 |
| 15-05 | H | H | COCH3 | H | H | −12.45 | −11.99 | 58 |
| 15-06 | CH3 | H | COCH3 | H | CH3 | −13.33 | −12.99 | 85 |
| 15-07 | H | H | COOCH3 | H | H | −12.13 | −11.57 | 35 |
| 15-08 | CH3 | H | COOCH3 | H | CH3 | −13.08 | −12.55 | 55 |
| 15-09 | H | H | CN | H | H | −12.18 | −11.81 | 132 |
| 15-10 | CH3 | H | CN | H | CH3 | −13.08 | −12.89 | 126 |
| 15-11 | H | F | CN | H | H | −12.45 | −11.84 | 70 |
| 15-12 | H | F | CN | F | H | −12.46 | −11.67 | 49 |
| 15-13 | H | CH3 | H | CH3 | H | −11.69 | −11.13 | 21 |
| 15-14 | Br | H | CHO | H | Br | −13.55 | −13.29 | 103 |
| 15-15 | H | H | OH | H | H | −11.13 | −10.90 | 12 |
| 15-16 | H | OH | H | OH | H | −10.65 | −10.37 | 21 |

TABLE 16

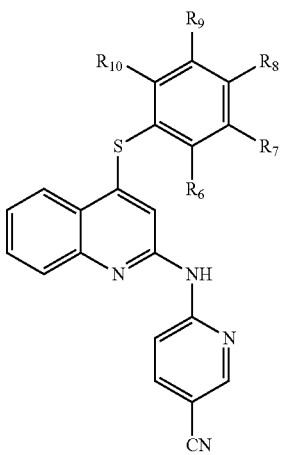

| Entry | R6 | R7 | R8 | R9 | R10 | BE | ABE | NOC |
|---|---|---|---|---|---|---|---|---|
| 16-01 | H | H | CHO | H | H | −11.38 | −11.04 | 89 |
| 16-02 | CH3 | H | CHO | H | CH3 | −12.41 | −11.95 | 123 |
| 16-03 | H | H | COOH | H | H | −10.94 | −10.50 | 3 |
| 16-04 | CH3 | H | COOH | H | CH3 | −11.72 | −11.07 | 107 |
| 16-05 | H | H | COCH3 | H | H | −11.92 | −11.37 | 71 |
| 16-06 | CH3 | H | COCH3 | H | CH3 | −12.99 | −12.34 | 97 |
| 16-07 | H | H | COOCH3 | H | H | −11.77 | −10.95 | 59 |
| 16-08 | CH3 | H | COOCH3 | H | CH3 | −12.89 | −12.03 | 87 |
| 16-09 | H | H | CN | H | H | −11.82 | −11.45 | 103 |
| 16-10 | CH3 | H | CN | H | CH3 | −12.71 | −12.28 | 121 |
| 16-11 | H | F | CN | H | H | −12.02 | −11.34 | 82 |
| 16-12 | H | F | CN | F | H | −12.01 | −11.49 | 78 |
| 16-13 | H | CH3 | H | CH3 | H | −12.27 | −11.65 | 64 |
| 16-14 | Br | H | CHO | H | Br | −13.40 | −12.87 | 113 |
| 16-15 | H | H | OH | H | H | −11.24 | −10.88 | 30 |
| 16-16 | H | OH | H | OH | H | −11.14 | −10.85 | 11 |

TABLE 17

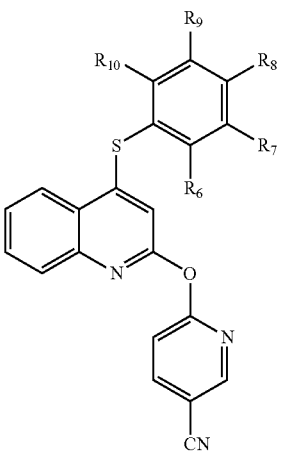

| Entry | R6 | R7 | R8 | R9 | R10 | BE | ABE | NOC |
|---|---|---|---|---|---|---|---|---|
| 17-01 | H | H | CHO | H | H | −11.42 | −11.13 | 48 |
| 17-02 | CH3 | H | CHO | H | CH3 | −12.18 | −11.73 | 108 |
| 17-03 | H | H | COOH | H | H | −11.00 | −10.69 | 27 |
| 17-04 | CH3 | H | COOH | H | CH3 | −11.59 | −10.86 | 99 |
| 17-05 | H | H | COCH3 | H | H | −11.78 | −11.14 | 26 |
| 17-06 | CH3 | H | COCH3 | H | CH3 | −12.74 | −12.13 | 97 |
| 17-07 | H | H | COOCH3 | H | H | −11.48 | −10.75 | 54 |
| 17-08 | CH3 | H | COOCH3 | H | CH3 | −12.57 | −11.75 | 77 |
| 17-09 | H | H | CN | H | H | −11.62 | −11.42 | 108 |
| 17-10 | CH3 | H | CN | H | CH3 | −12.55 | −12.16 | 111 |
| 17-11 | H | F | CN | H | H | −12.05 | −11.45 | 67 |
| 17-12 | H | F | CN | F | H | −11.92 | −11.34 | 78 |
| 17-13 | H | CH3 | H | CH3 | H | −12.06 | −11.48 | 65 |
| 17-14 | Br | H | CHO | H | Br | −13.08 | −12.66 | 107 |
| 17-15 | H | H | OH | H | H | −11.45 | −10.98 | 39 |
| 17-16 | H | OH | H | OH | H | −11.27 | −10.86 | 17 |

TABLE 18

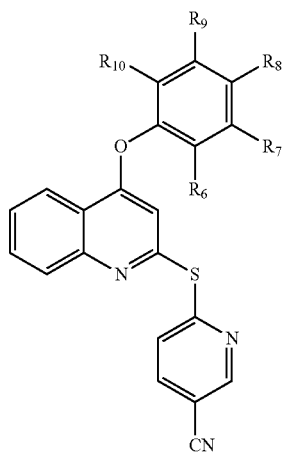

| Entry | $R_6$ | $R_7$ | $R_8$ | $R_9$ | $R_{10}$ | BE | ABE | NOC |
|---|---|---|---|---|---|---|---|---|
| 18-01 | H | H | CHO | H | H | −11.35 | −11.02 | 115 |
| 18-02 | $CH_3$ | H | CHO | H | $CH_3$ | −12.15 | −11.82 | 130 |
| 18-03 | H | H | COOH | H | H | −10.94 | −10.35 | 81 |
| 18-04 | $CH_3$ | H | COOH | H | $CH_3$ | −11.48 | −10.96 | 111 |
| 18-05 | H | H | $COCH_3$ | H | H | −12.12 | −11.39 | 101 |
| 18-06 | $CH_3$ | H | $COCH_3$ | H | $CH_3$ | −12.67 | −12.15 | 116 |
| 18-07 | H | H | $COOCH_3$ | H | H | −11.84 | −10.99 | 68 |
| 18-08 | $CH_3$ | H | $COOCH_3$ | H | $CH_3$ | −12.52 | −11.80 | 84 |
| 18-09 | H | H | CN | H | H | −11.85 | −11.46 | 116 |
| 18-10 | $CH_3$ | H | CN | H | $CH_3$ | −12.51 | −12.26 | 137 |
| 18-11 | H | F | CN | H | H | −12.31 | −11.75 | 103 |
| 18-12 | H | F | CN | F | H | −12.35 | −11.84 | 87 |
| 18-13 | H | $CH_3$ | H | $CH_3$ | H | −12.02 | −10.96 | 62 |
| 18-14 | Br | H | CHO | H | Br | −12.91 | −12.47 | 127 |
| 18-15 | H | H | OH | H | H | −11.13 | −10.69 | 33 |
| 18-16 | H | OH | H | OH | H | −11.26 | −10.52 | 29 |

TABLE 19

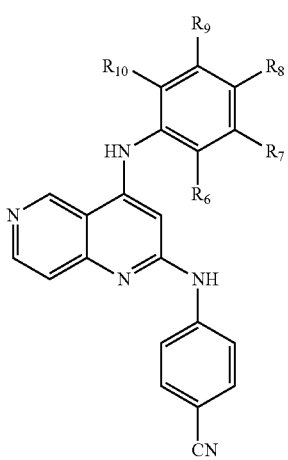

| Entry | $R_6$ | $R_7$ | $R_8$ | $R_9$ | $R_{10}$ | BE | ABE | NOC |
|---|---|---|---|---|---|---|---|---|
| 19-01 | H | H | CHO | H | H | −11.98 | −11.77 | 82 |
| 19-02 | $CH_3$ | H | CHO | H | $CH_3$ | −12.71 | −12.55 | 125 |
| 19-03 | H | H | COOH | H | H | −11.54 | −11.17 | 53 |
| 19-04 | $CH_3$ | H | COOH | H | $CH_3$ | −12.21 | −11.92 | 101 |
| 19-05 | H | H | $COCH_3$ | H | H | −12.47 | −12.12 | 65 |
| 19-06 | $CH_3$ | H | $COCH_3$ | H | $CH_3$ | −13.43 | −13.09 | 93 |
| 19-07 | H | H | $COOCH_3$ | H | H | −12.14 | −11.45 | 22 |
| 19-08 | $CH_3$ | H | $COOCH_3$ | H | $CH_3$ | −13.18 | −12.54 | 61 |
| 19-09 | H | H | CN | H | H | −12.36 | −12.13 | 136 |
| 19-10 | $CH_3$ | H | CN | H | $CH_3$ | −13.13 | −12.96 | 126 |
| 19-11 | H | F | CN | H | H | −12.47 | −12.14 | 91 |
| 19-12 | H | F | CN | F | H | −12.41 | −11.89 | 77 |
| 19-13 | H | $CH_3$ | H | $CH_3$ | H | −11.71 | −11.05 | 54 |
| 19-14 | Br | H | CHO | H | Br | −13.57 | −13.39 | 114 |
| 19-15 | H | H | OH | H | H | −11.08 | −10.89 | 80 |
| 19-16 | H | OH | H | OH | H | −11.12 | −10.86 | 65 |

TABLE 20

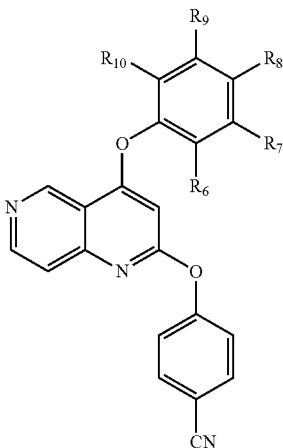

| Entry | $R_6$ | $R_7$ | $R_8$ | $R_9$ | $R_{10}$ | BE | ABE | NOC |
|---|---|---|---|---|---|---|---|---|
| 20-01 | H | H | CHO | H | H | −11.92 | −11.72 | 86 |
| 20-02 | $CH_3$ | H | CHO | H | $CH_3$ | −12.57 | −12.37 | 113 |
| 20-03 | H | H | COOH | H | H | −11.50 | −11.34 | 47 |
| 20-04 | $CH_3$ | H | COOH | H | $CH_3$ | −12.11 | −11.72 | 107 |
| 20-05 | H | H | $COCH_3$ | H | H | −12.36 | −12.09 | 84 |
| 20-06 | $CH_3$ | H | $COCH_3$ | H | $CH_3$ | −13.28 | −12.89 | 119 |
| 20-07 | H | H | $COOCH_3$ | H | H | −11.91 | −11.29 | 41 |
| 20-08 | $CH_3$ | H | $COOCH_3$ | H | $CH_3$ | −12.94 | −12.26 | 80 |
| 20-09 | H | H | CN | H | H | −12.14 | −11.96 | 121 |
| 20-10 | $CH_3$ | H | CN | H | $CH_3$ | −13.02 | −12.80 | 125 |
| 20-11 | H | F | CN | H | H | −12.41 | −12.11 | 101 |
| 20-12 | H | F | CN | F | H | −12.40 | −11.97 | 82 |
| 20-13 | H | $CH_3$ | H | $CH_3$ | H | −11.56 | −11.11 | 36 |
| 20-14 | Br | H | CHO | H | Br | −13.41 | −13.15 | 128 |
| 20-15 | H | H | OH | H | H | −11.09 | −10.93 | 95 |
| 20-16 | H | OH | H | OH | H | −11.40 | −10.99 | 69 |

TABLE 21

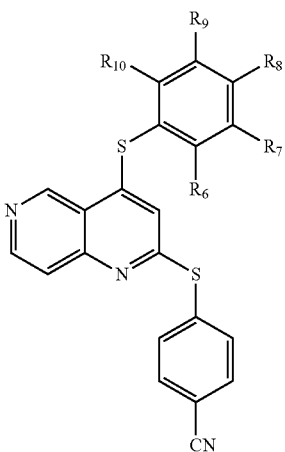

| Entry | R$_6$ | R$_7$ | R$_8$ | R$_9$ | R$_{10}$ | BE | ABE | NOC |
|---|---|---|---|---|---|---|---|---|
| 21-01 | H | H | CHO | H | H | −11.45 | −11.14 | 89 |
| 21-02 | CH$_3$ | H | CHO | H | CH$_3$ | −11.81 | −11.36 | 19 |
| 21-03 | H | H | COOH | H | H | −10.92 | −10.60 | 53 |
| 21-04 | CH$_3$ | H | COOH | H | CH$_3$ | −11.43 | −10.72 | 34 |
| 21-05 | H | H | COCH$_3$ | H | H | −12.06 | −11.59 | 59 |
| 21-06 | CH$_3$ | H | COCH$_3$ | H | CH$_3$ | −12.26 | −11.49 | 17 |
| 21-07 | H | H | COOCH$_3$ | H | H | −11.91 | −11.31 | 39 |
| 21-08 | CH$_3$ | H | COOCH$_3$ | H | CH$_3$ | −12.09 | −10.77 | 11 |
| 21-09 | H | H | CN | H | H | −11.81 | −11.47 | 117 |
| 21-10 | CH$_3$ | H | CN | H | CH$_3$ | −12.12 | −11.36 | 21 |
| 21-11 | H | F | CN | H | H | −12.02 | −11.54 | 86 |
| 21-12 | H | F | CN | F | H | −11.33 | −10.99 | 16 |
| 21-13 | H | CH$_3$ | H | CH$_3$ | H | −12.29 | −11.88 | 80 |
| 21-14 | Br | H | CHO | H | Br | −12.19 | −11.61 | 42 |
| 21-15 | H | H | OH | H | H | −11.14 | −10.83 | 9 |
| 21-16 | H | OH | H | OH | H | −10.98 | −10.59 | 8 |

TABLE 22

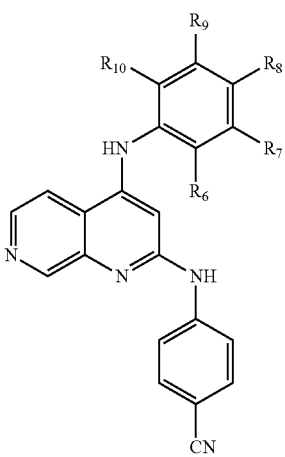

| Entry | R$_6$ | R$_7$ | R$_8$ | R$_9$ | R$_{10}$ | BE | ABE | NOC |
|---|---|---|---|---|---|---|---|---|
| 22-01 | H | H | CHO | H | H | −11.83 | −11.62 | 74 |
| 22-02 | CH$_3$ | H | CHO | H | CH$_3$ | −12.77 | −12.61 | 112 |
| 22-03 | H | H | COOH | H | H | −11.35 | −11.07 | 79 |
| 22-04 | CH$_3$ | H | COOH | H | CH$_3$ | −12.30 | −12.07 | 101 |
| 22-05 | H | H | COCH$_3$ | H | H | −12.54 | −12.19 | 55 |
| 22-06 | CH$_3$ | H | COCH$_3$ | H | CH$_3$ | −13.49 | −13.13 | 81 |
| 22-07 | H | H | COOCH$_3$ | H | H | −12.29 | −11.68 | 40 |
| 22-08 | CH$_3$ | H | COOCH$_3$ | H | CH$_3$ | −13.23 | −12.75 | 55 |
| 22-09 | H | H | CN | H | H | −12.26 | −11.94 | 136 |
| 22-10 | CH$_3$ | H | CN | H | CH$_3$ | −13.21 | −13.03 | 125 |
| 22-11 | H | F | CN | H | H | −12.53 | −11.95 | 73 |
| 22-12 | H | F | CN | F | H | −12.40 | −11.75 | 61 |
| 22-13 | H | CH$_3$ | H | CH$_3$ | H | −11.73 | −11.36 | 28 |
| 22-14 | Br | H | CHO | H | Br | −13.63 | −13.44 | 117 |
| 22-15 | H | H | OH | H | H | −11.16 | −10.91 | 14 |
| 22-16 | H | OH | H | OH | H | −10.90 | −10.44 | 6 |

TABLE 23

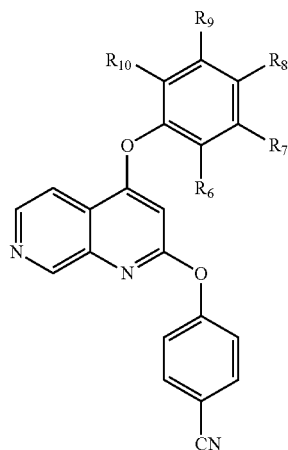

| Entry | R$_6$ | R$_7$ | R$_8$ | R$_9$ | R$_{10}$ | BE | ABE | NOC |
|---|---|---|---|---|---|---|---|---|
| 23-01 | H | H | CHO | H | H | −11.55 | −11.40 | 75 |
| 23-02 | CH$_3$ | H | CHO | H | CH$_3$ | −12.63 | −12.41 | 116 |
| 23-03 | H | H | COOH | H | H | −11.02 | −10.80 | 62 |
| 23-04 | CH$_3$ | H | COOH | H | CH$_3$ | −12.14 | −11.88 | 107 |
| 23-05 | H | H | COCH$_3$ | H | H | −12.24 | −11.94 | 70 |
| 23-06 | CH$_3$ | H | COCH$_3$ | H | CH$_3$ | −13.32 | −12.96 | 97 |
| 23-07 | H | H | COOCH$_3$ | H | H | −11.99 | −11.27 | 40 |
| 23-08 | CH$_3$ | H | COOCH$_3$ | H | CH$_3$ | −13.09 | −12.49 | 89 |
| 23-09 | H | H | CN | H | H | −11.98 | −11.66 | 124 |
| 23-10 | CH$_3$ | H | CN | H | CH$_3$ | −13.06 | −12.85 | 126 |
| 23-11 | H | F | CN | H | H | −12.33 | −11.96 | 116 |
| 23-12 | H | F | CN | F | H | −12.45 | −11.78 | 83 |
| 23-13 | H | CH$_3$ | H | CH$_3$ | H | −11.65 | −11.08 | 30 |
| 23-14 | Br | H | CHO | H | Br | −13.47 | −13.16 | 106 |
| 23-15 | H | H | OH | H | H | −10.99 | −10.59 | 23 |
| 23-16 | H | OH | H | OH | H | −11.02 | −10.40 | 30 |

TABLE 24

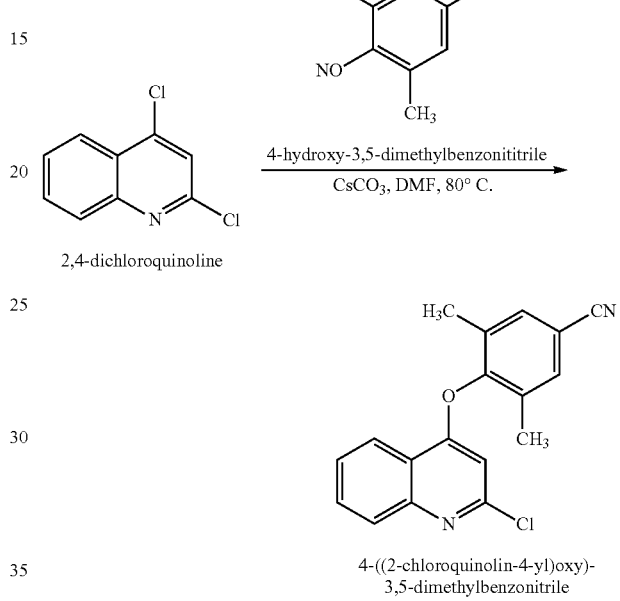

| Entry | R6 | R7 | R8 | R9 | R10 | BE | ABE | NOC |
|---|---|---|---|---|---|---|---|---|
| 24-01 | H | H | CHO | H | H | −11.48 | −11.21 | 78 |
| 24-02 | CH3 | H | CHO | H | CH3 | −12.32 | −11.67 | 19 |
| 24-03 | H | H | COOH | H | H | −10.96 | −10.69 | 68 |
| 24-04 | CH3 | H | COOH | H | CH3 | −11.59 | −10.89 | 5 |
| 24-05 | H | H | COCH3 | H | H | −12.05 | −11.62 | 71 |
| 24-06 | CH3 | H | COCH3 | H | CH3 | −12.65 | −11.98 | 11 |
| 24-07 | H | H | COOCH3 | H | H | −11.91 | −11.29 | 31 |
| 24-08 | CH3 | H | COOCH3 | H | CH3 | −11.94 | −10.91 | 7 |
| 24-09 | H | H | CN | H | H | −11.85 | −11.40 | 12 |
| 24-10 | CH3 | H | CN | H | CH3 | −12.84 | −11.81 | 17 |
| 24-11 | H | F | CN | H | H | −12.05 | −11.58 | 74 |
| 24-12 | H | F | CN | F | H | −11.43 | −10.62 | 49 |
| 24-13 | H | CH3 | H | CH3 | H | −12.23 | −11.87 | 85 |
| 24-14 | Br | H | CHO | H | Br | −12.24 | −11.99 | 9 |
| 24-15 | H | H | OH | H | H | −11.11 | −10.75 | 11 |
| 24-16 | H | OH | H | OH | H | −10.93 | −10.68 | 11 |

BE is the estimated free energy of binding.
ABE is the mean energy of binding.
NOC is the number of conformations in this cluster.

The compounds of the present invention can be synthesized through various methods. The starting materials and reagents used in the synthesis are available from commercial suppliers or may be prepared through well-known methods. The following synthetic reaction scheme as scheme 1 is merely an illustration of one method for synthesizing a compound of the present invention. The preparations of the compounds of in the following examples are not intended to limit the scope of the invention. Various modifications to the synthetic reaction scheme should be included in the scope of the present invention.

The precursors and intermediates of the synthetic reaction scheme can be isolated and purified through conventional techniques, such as filtration, distillation, crystallization, and chromatography. Similarly, characterization of such materials can be performed using conventional means, including physical constants and spectral data.

Unless specified to the contrary, the reaction described herein preferably is conducted under an inert atmosphere at atmospheric pressure at a reaction temperature range of from about 50° C. to about 150° C., more preferably from about 80° C. to about 120° C., and the most preferably and conveniently at about 120° C. The reaction condition is exemplary.

In general, the nomenclature used in the description is based on ChambridgeSoft™ v. 12.0 for the generation of IUPAC systematic nomenclature. If a discrepancy exists between a depicted structure and its name, the depicted structure is to be accorded more weight.

Meanwhile, 4-((2-((4-Cyanophenyl)amino)quinoline-4-yl)oxy)-3,5-dimethylbenzonitrile is prepared in 30% yield by coupling 2,4-dichloroquinoline with 4-hydroxy-3,5-dimethylbenzonitrile. The final compound is obtained from the nucleophilic substitution reaction of 4-((2-chloroquinolin-4-yl)oxy)-3,5-dimethylbenzonitrile with 4-aminobenzonitrile (Scheme 1).

Scheme 1: Method for the preparation of 4-((2-((4-cyanophenyl)amino)quinoline-4-yl)oxy)-3,5-dimethylbenzonitrile.

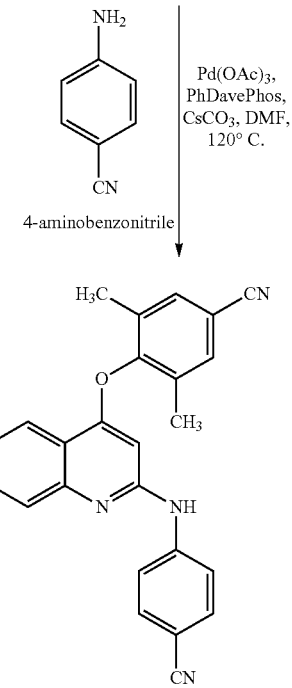

Example 1: Synthesis of 4-((2-chloroquinolin-4-yl)oxy)-3,5-dimethylbenzonitrile 4-Hydroxy-3,5-dimethylbenzonitrile (247 mg) and cesium carbonate (100 mg) were added to a solution of 2,4-dichloroquinoline (300 mg) in redistilled DMF (15 mL). The mixture was stirred at 80° C. under Argon protection. After the reaction, thin layer chromatography was performed until its completion. $H_2O$ with ice (50 mL) was added, and the aqueous solution was extracted with EtOAc (3×15 mL). The combined organic layer was washed with saturated brine (20 mL), dried over anhydrous $Na_2SO_4$, and then filtered and concentrated under reduced pressure. The residue was purified via column chromatography in which 10% EtOAc/hexane was used to obtain the target compound (280 mg; 59% yield).

Example 2: Synthesis of 4-((2-((4-cyanophenyl)amino)quinoline-4-yl)oxy)-3,5-dimethylbenzonitrile $Pd(OAc)_2$ (5 mg) and PhDavePhos (8.6 mg) were added to a solution of 4-((2-chloroquinolin-4-yl)oxy)-3,5-dimethylbenzonitrile (70 mg) and 4-aminobenzonitrile (35 mg) in redistilled DMF (5 mL). The mixture was stirred at 120° C. under Argon protection. After the reaction, thin layer chromatography was performed until its completion. $H_2O$ with ice (50 mL) was added, and the aqueous solution was extracted with EtOAc (3×15 mL). The combined organic layer was washed with saturated brine (20 mL), dried over anhydrous $Na_2SO_4$, filtered, and then concentrated under reduced pressure. The residue was purified via column chromatography using 15% EtOAc/hexane to obtain the target compounds (45 rag; 51% yield).

The pharmaceutical compositions of the present invention comprise a compound based on the invention and one or more pharmaceutically acceptable carriers, excipients, or diluents. Other therapeutic agents are optional. Pharmaceutical compositions containing a compound based on the invention as active ingredient may be in any form suitable for the intended method of administration. When applied for oral use, tablets, troches, lozenges, aqueous or oil suspensions, dispersible powders or granules, emulsions, hard or soft capsules, syrups, or elixirs may be prepared. Compositions intended for oral use may be prepared through any conventional method for the manufacture of pharmaceutical compositions, which may contain one or more agents, such as antioxidants, sweetening agents, flavoring agents, coloring agents, and preserving agents, to provide a palatable preparation. Tablets containing an active ingredient in the admixture with pharmaceutically acceptable nontoxic excipients, which are suitable for the manufacture of tablets, are acceptable. These excipients may be inert diluents, such as calcium or sodium carbonate, lactose, lactose monohydrate, croscarmellose sodium, povidone, calcium, or sodium phosphate; granulating and disintegrating agents, such as maize starch or alginic acid; binding agents, such as cellulose, microcrystalline cellulose, starch, gelatin, or acacia; and lubricating agents, such as magnesium stearate, stearic acid, or talc. Tablets may be uncoated or coated by conventional techniques, such as microencapsulation, to delay disintegration and absorption in the gastrointestinal tract and thereby provide a sustained action over a long period.

The drug intended for oral use may be also presented as hard gelatin capsules, in which the active ingredient is mixed with an inert solid diluent, such as pregelatinized starch, calcium phosphate, or kaolin; or as soft gelatin capsules, in which the active ingredient is mixed with water or an oil medium, such as peanut oil, liquid paraffin, or olive oil.

Aqueous and oil suspensions of the invention contain the active materials in the admixture with excipients suitable for the manufacture of aqueous suspensions. Such excipients include a suspending agents, such as sodium carboxymethylcellulose, methylcellulose, hydroxypropyl methylcellulose, sodium alginate, polyvinylpyrrolidone, gum tragacanth, and gum acacia; and dispersing or wetting agents, such as naturally occurring phosphatide (e.g., lecithin), a condensation product of alkylene oxide with a fatty acid (e.g., polyoxyethylene stearate), a condensation product of ethylene oxide with a long chain of aliphatic alcohol (e.g., heptadecaethyleneoxycetanol), and a condensation product of ethylene oxide with a partial ester derived from a fatty acid and hexitol anhydride (e.g., polyoxyethylene sorbitan monooleate).

The aqueous suspension may also contain one or more preservatives (ethyl or n-propyl p-hydroxybenzoate), coloring agents, flavoring agents, and sweetening agents (such as sucrose, sucralose, or saccharin).

Oil suspensions may be formulated by suspending the active ingredient in vegetable oil, such as arachis oil, olive oil, sesame oil, or coconut oil, or in mineral oil, such as liquid paraffin. The oral suspensions may contain a thickening agent, such as beeswax, hard paraffin, or cetyl alcohol. Sweetening agents and flavoring agents may be added to provide a palatable oral preparation. These compositions may be preserved with the addition of an antioxidant, such as ascorbic acid and butylated hydroxytoluene (BHT).

The pharmaceutical compositions of the invention may be in the form of a sterile injectable preparation, such as a sterile injectable aqueous or oleaginous suspension. This suspension may be formulated through methods in which suitable dispersing or wetting agents and suspending agents are used. The sterile injectable preparation may also be a sterile injectable solution or suspension in a nontoxic, parenterally acceptable diluent or solvent, such as a solution in 1,3-butane-diol or prepared as a lyophilized powder. Among the acceptable vehicles and solvents that may be employed are water, Ringer's solution, and isotonic sodium chloride solution. In addition, sterile fixed oils may be used as solvents or suspending media. For this purpose, any bland fixed oil, including synthetic mono- or diglycerides; may be employed. Fatty acids such as oleic acid may also be used in the preparation of injectables.

The pharmaceutical compositions of the invention may be injected parenterally. In particular, they may be injected intravenously, intraperitoneally, intrathecally, intraventricularly, intrasternally, intracranially, intramuscularly, or subcutaneously. They may also be administered via infusion techniques. They are used in the form of a sterile aqueous solution, which may contain other substances, such as salts or glucose, to make the solution isotonic with blood. The aqueous solutions should be suitably buffered, if necessary.

The preparation of suitable parenteral formulations under sterile conditions is readily accomplished via standard pharmaceutical techniques.

Dispersible powders and granules of the invention suitable for the preparation of an aqueous suspension with the addition of water provide the active ingredient in admixture with a dispersing or wetting agent, a suspending agent, and one or more preservatives. Additional excipients, such as sweetening, flavoring, and coloring agents, may also be present.

A combination of the compound according to the invention and other ARV agent(s) for treating or preventing HIV infection is also provided.

For the purpose of the present invention, other ARV drugs/agents or anti-HIV agents may be selected from nucleoside and nucleotide reverse transcription inhibitors (NRTIs), NNRTIs, protease inhibitors (PIs), maturation inhibitors (MIs), and any of their combinations. The term "nucleoside and NRTIs" used in the preset study refers to the nucleosides, nucleotides and their analogues that inhibit the activity of HIV-1 RT, which catalyzes the conversion of viral genomic HIV-1 RNA into proviral HIV-1 DNA.

NRTIs that may be employed in the combination with the present invention may comprise zidovudine; didanosine; stavudine; lamivudine; abacavir; adefovir; lobucavir; entecavir; apricitabine; emtricitabine; zalcitabine; dexelvucitabine; alovudine; andoxovir; elvucitabine; AVX754; BCH-189; phosphazid; racivir; SP 1093V; stampidine; BCH-10652, p-L-FD4 (also called -L-D4C and named P-L-2',3'-dicleoxy-5-fluoro-cytidene); DAPD, the purine nucleoside, (−)-P-D-2,6-diamino-purine dioxolane; lodenosine (FddA), 9-(2,3-dideoxy-2-fluoro-D-threo-pentofiiranosyl)adenine; and any combination thereof.

NRTIs that may be employed in pharmaceutical composition of the present invention may comprise tenofovir, adefovir, emtricitabine, lamivudine, zidovudine, or any of their combinations.

NNRTIs that may be employed in combination of the present invention may comprise nevirapine, rilpivirine, delaviridine, efavirenz, and ETR. Other NNRTIs include PNU-142721, fiiropyridine-thiopyrimide; capravirine (S-1153 or AG-1 549; 5-(3,5-dichlorophenyl)-thio-4-isopropyl-1-(4-pyridyl)methyl-1H-imidazol-2-ylmethyl carbonate); emivirine [MKC-442; (1-(ethoxy-memyl)-5-(1-methylethyl)-6-(phenylmethyl)-(2,4(1H,3H)-pyrimid-inedione)]; (+)-calanolide A (NSC-67545 1) and B, coumarin derivatives; DAPY (TMC120; 4-{4-[4-((E)-2-cyano-vinyl)-2,6-dimethyl-phenylamino]-pyrimidin-2-ylamino-}-benzonitrile); BILR-355 BS (12-ethyl-8-[2-(1-hydroxy-quinolin-4-yloxy)-ethyl]-5-methyl-1 1,12-dihydro~5H-1,5, 10, 12-tetraaza-dibenzo[a,e]cycloocten-6-one; and PHI-236 (7-bromo-3-[2-(2,5-dimethoxy-phenyl)-ethyl]-3,4-dihydro-1H-pyrido[1,2-a][-1,3,5]triazine-2-thione) and PHI-443 (TMC-278, 1-(5-bromo-pyridin-2-yl)-3-(2-thiophen-2-yl-ethyl)-thio urea).

PIs that may be employed in the pharmaceutical composition of the present invention may comprise saquinavir; ritonavir; nelfinavir; amprenavir; lopinavir, indinavir; nelfinavir; atazanavir lasinavir; palinavir; tipranavir; fosamprenavir; darunavir; TMC114; DMP450, a cyclic urea; BMS-2322623, BMS-232623; GS3333; KNI-413; KNI-272; LG-71350; CGP-61755; PD 173606; PD 177298; PD 178390; PD 178392; U-140690; ABT-378; and AG-1549, an imidazole carbamate. Additional PIs include N-cycloalkylglycines, α-hydroxyaryl butanamides; α-hydroxy-β-[[(carbocyclic- or heterocyclic-substituted)amino)carbonyl] alkanamide derivatives; γ-hydroxy-2-(fluoroalkylaminocarbonyl)-1-piperazine pentanamides; dihydropyrone derivatives and α- and β-amino acid hydroxyethylaminosulfonamides; and N-amino acid substituted L-lysine derivatives.

ARV agents may be used in the form of salts or esters derived from inorganic or organic acids.

A combination of the compound according to the invention and other chemotherapeutic agents(s) for treating or preventing HIV infection is also provided.

Other chemotherapeutic agents, such as vinca alkaloids, agents that disrupt microtubule formation (e.g., colchicines and its derivatives), anti-angiogenic agents, therapeutic antibodies, EGFR targeting agents, tyrosine kinase targeting agents (e.g., tyrosine kinase inhibitors), transitional metal complexes, proteasome inhibitors, antimetabolites (e.g., nucleoside analogs), alkylating agents, platinum-based agents, anthracycline antibiotics, topoisomerase inhibitors, macrolides, therapeutic antibodies, retinoids (e.g., all-trans retinoic acids or a derivative thereof), geldanamycin or a derivative thereof (e.g., 17-AAG), and other standard chemotherapeutic agents.

Other chemotherapeutic agents may comprise adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof), topetecan, vinblastine, vincristine, tamoxifen, piposulfan, nab-5404, nab-5800, nab-5801, Irinotecan, HKP, Ortataxel, gemcitabine, Herceptin®, vinorelbine, Doxil®, capecitabine, Alimta®, Avastin®, Velcade®, Tarceva®, Neulasta®, Lapatinib, Sorafenib, derivatives thereof, chemotherapeutic agents known in the art, and the like.

Other chemotherapeutic agents may comprise a antineoplastic agent, such as carboplatin, Navelbine® (vinorelbine), anthracycline (Doxil®), lapatinib (GW57016), Herceptin®, gemcitabine (Gemzar®), capecitabine (Xeloda®), Alimta®, cisplatin, 5-fluorouracil, epirubicin, cyclophosphamide, Avastin®, and Velcade®.

Other chemotherapeutic agents may comprise antagonists, such as EGFR, ErbB2 (also known as Herb), ErbB3, ErbB4, and TNF, which are involved in tumor growth.

These chemotherapeutic agents apply to chemotherapeutic agents or their derivatives or analogs.

Table 25 shows some examples of evaluated representative compounds that have inhibitory effects on HIV infection and cancer proliferation. Their inhibitory results are provided in Tables 26-27 for reference. They should not be considered as a limitation to the scope of the invention but merely as illustrations and representations.

TABLE 25

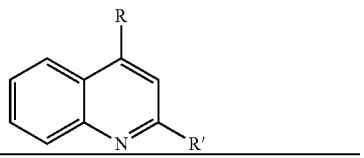

| Entry | R' | R |
|---|---|---|
| 1 | 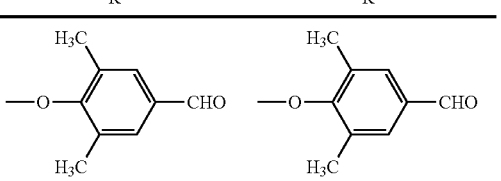 | 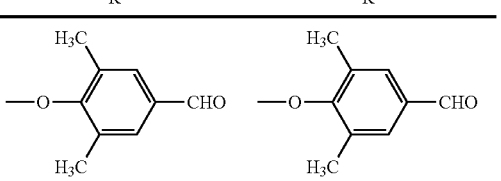 |
| 2 | 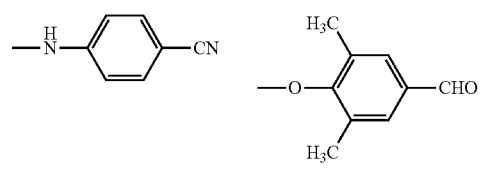 | 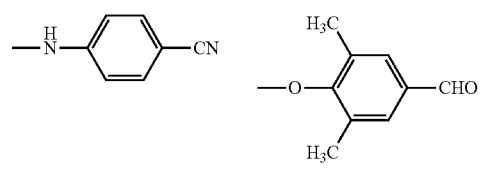 |
| 3 | 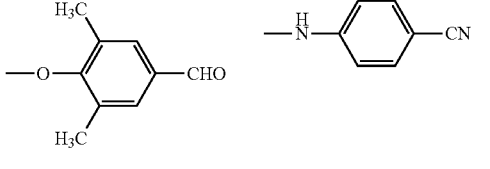 | 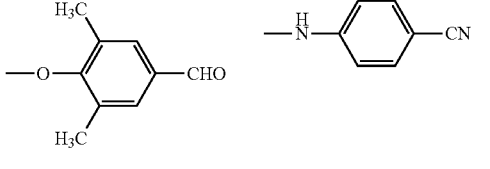 |
| 4 | 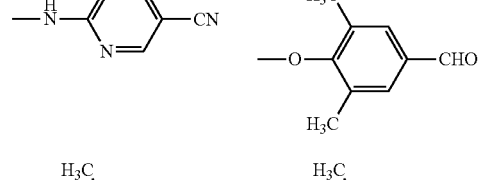 | 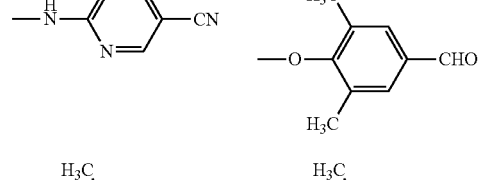 |
| 5 | 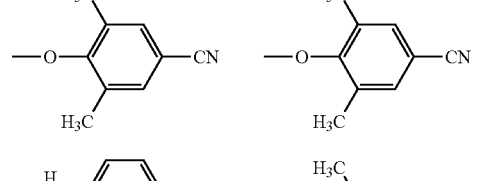 | 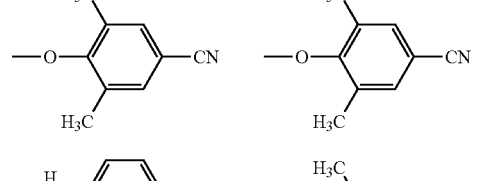 |
| 6 | 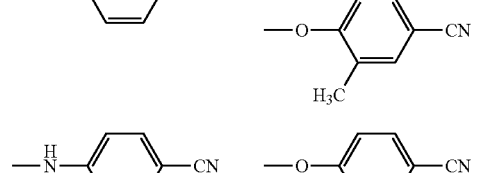 | 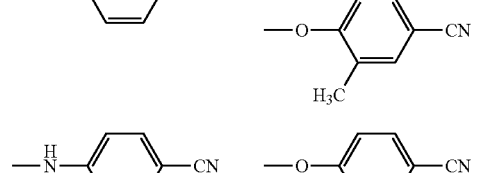 |
| 7 | 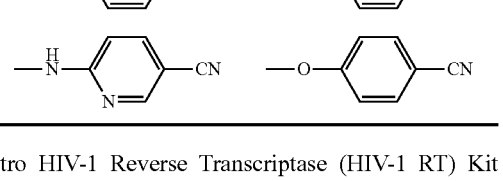 | 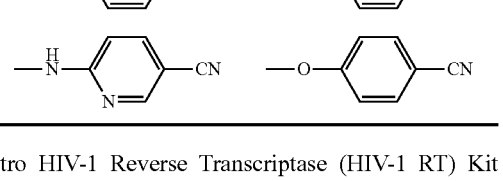 |
| 8 | —NH—⟨pyridine⟩—CN | —O—⟨phenyl⟩—CN |

In Vitro HIV-1 Reverse Transcriptase (HIV-1 RT) Kit Assay

The HIV-RT inhibition assay was performed using an RT assay kit (Roche) according to the protocol of the kit. Briefly, the reaction mixture consisted of template/primer complex, 2/-deoxy-nucleotide-5/-triphosphates (dNTPs) and RT enzyme in the lysis buffer with or without inhibitors. After 1 h of incubation at 37° C., the reaction mixture was transferred to a streptavidine-coated microtiter plate (MTP). Biotin-labeled dNTPs were incorporated in the template, because of the activity of RT bound to steptavidine. The unbound dNTPs were washed with wash buffer, and anti-digoxigenin-peroxidase (anti-DIG-POD) was added to the MTP. The digoxigenin-labeled dNTPs incorporated in the template was bound to the anti-DIG-POD antibody. The unbound anti-DIG-POD was washed, and the peroxide substrate (ABST) was added to the MTP. A colored reaction product was produced during the cleavage of the substrate catalyses with a peroxide enzyme. The absorbance of the sample was determined at OD 405 nM using a microtiter plate ELISA reader. The resulting color intensity was directly proportional to the actual RT activity. The percentage inhibitory activity of the RT inhibitors was calculated by comparing it to that of the sample without an inhibitor.

The HIV-1 RT inhibitory activity of compounds 1-8 in Table 25 was preliminarily evaluated by determining their percentage inhibition of HIV-RT activity in the HIV-1-RT kit in comparison with those of NVP, EFV, and rilpivirine. The results are shown in Table 26.

TABLE 26

Inhibitory activity of compounds 1-8, Nevirapine, Efavirenz, Rilpivirine against HIV-1 RT

| Entry | Inhibition rate (%) (HIV-RT kit assay) (1 µM) |
|---|---|
| 1 | 42.08 |
| 2 | 43.37 |
| 3 | 39.62 |
| 4 | 62.23 |
| 5 | 40.31 |
| 6 | 47.16 |
| 7 | 39.71 |
| 8 | 27.61 |
| Nevirapine | 55.58 |
| Efavirenz | 96.20 |
| Rilpivirine | 96.48 |

Cytotoxic Activity

Cell lines were seeded in a 96-well microplate (Costar No. 3599, USA) at 100 µL/well and density of $5 \times 10^3$-$2 \times 10^4$ cells/well. Background control wells contained the same volume of the complete culture medium. The microplate was incubated for 24 h at 37° C., 5% $CO_2$, and 95% humidity (Shellab, USA). Samples at various concentrations were added to the microplate, which was incubated for another 48 h. Cell viability was determined by staining with MTT assay [3(4,5-dimethylthiazol-2-yl)-2-5diphenyl tetrazolium bromide (Sigma-Aldrich, St. Louis, Mo., USA)]. The reagent was dissolved in phosphate buffered saline at 5 mg/mL and filtered to sterilize and remove the small amount of insoluble residue present in some batches of MTT. MTT solution (10 µL/100 µL medium) was added to all wells of each assay, and plates were incubated at 37° C., 5% $CO_2$, and 95% humidity for 2-4 h. Subsequently, dimethyl sulfoxide (Merck, Germany) (100 µL) was added to dissolve the resulting formazan by using sonication. The plates were read on a microplate reader (Molecular Devices, CA, USA). OD was measured at testing wavelength of 550 nm and reference wavelength of 650 nm.

XTT assay (3'-[1-[(phenylamino)-carbonyl]-3,4-tetrazolium]-bis(4-methoxy-6-nitro)benzene-sulfonic acid hydrate) for suspension cells was performed for acute lymphoblastic leukemia (MOLT-3). Plates were incubated for 4 h after the addition of 50 µL of mixture containing 1 mg/mL of sample (5 mL) and 0.383 of mg/mL phenazine methosulfate (100 µL). The absorbance of the formed orange formazan compound was measured at wavelengths of 492 and 690 nm. $IC_{50}$ values were determined in the same manner as the drug and sample concentrations at 50% inhibition of cell growth.

The cytotoxic activity of compounds 1-8 shown in Table 25 was preliminarily evaluated by determining their cytotoxic activities against hepatocarcinoma, acute lymphoblastic leukemia, cholangiocarcinoma, and lung carcinoma. Their cytotoxic activities were then compared with those of etoposide and doxorubicin hydrochloride. The results are shown in Table 27.

TABLE 27

In vitro cytotoxic activity of tested compounds against human cancer cell lines[a]

| | $IC_{50}$ (µg/mL)[b] | | | |
|---|---|---|---|---|
| Entry | HepG2 | MOLT-3 | HuCCA-1 | A549 |
| 1 | 21.55 ± 5.23 | 2.62 ± 0.30 | 4.71 ± 0.30 | 16.37 ± 0.56 |
| 2 | 25.95 ± 2.40 | 4.63 ± 0.62 | 11.58 ± 0.77 | 20.13 ± 1.20 |
| 3 | 41.63 ± 6.80 | 8.76 ± 0.75 | ≥50 | ≥50 |
| 4 | 36.53 ± 4.65 | 4.98 ± 0.43 | 49.5 ± 0.71 | 42.44 ± 0.48 |
| 5 | 38.67 ± 2.87 | ≥50 | 35.02 ± 4.65 | 23.28 ± 2.40 |
| 6 | ≥50 | 19.04 ± 16.02 | ≥50 | ≥50 |
| 7 | ≥50 | ≥50 | ≥50 | ≥50 |
| 8 | 39.96 ± 0.26 | 5.12 ± 0.41 | 8.31 ± 0.33 | 5.09 ± 0.81 |
| Etoposide | 21.14 ± 0.70 | 0.048 ± 0.007 | N/A | N/A |
| Doxorubicin Hydrochloride | 0.23 ± 0.02 | N/A | 0.89 ± 0.04 | 0.19 ± 0.01 |

[a]HepG2 (Hepatocarcinoma), MOLT-3 (Acute lymphoblastic leukemia), HuCCA-1 (Cholangiocarcinoma), A549 (Lung carcinoma)

[b]Results are expressed as mean ± standard error of inhibition perceptual for all cell lines. Doxorubicin and etoposide were used as positive control. Experiments were performed in triplicate.

Docking Protocol

The docking studies were performed with autodock 4.2 as described by Olson et al. (Morris G M, Huey R, Lindstrom W, Sanner M F, Belew R K, Goodsell D S and Olson A J. J. Comput. Chem. 2009 16: 2785-91).

The invention claimed is:
1. A compound of the formula (I):

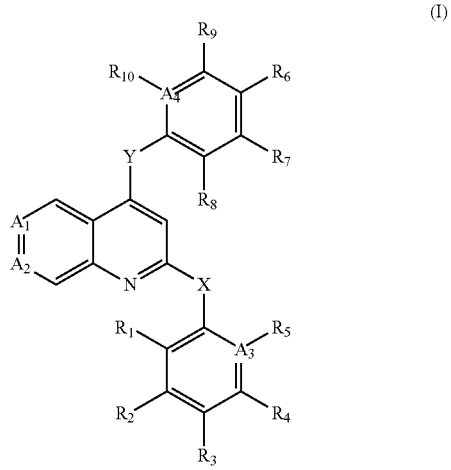

where

X and Y may be identical or different and represent O, NH, or S;

$R_1$, $R_2$, $R_3$, $R_4$, $R_5$, $R_6$, $R_7$, $R_8$, $R_9$, and $R_{10}$ may be identical or different and represent H, halogen, CN, $NO_2$, $(C_{1-4})$alkyl, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^B$, $C(O)R^A$, $CO_2R^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R^A$ and $R^B$ may be identical or different and represent H, $(C_{1-4})$alkyl, $(C_{1-4})$haloalkyl, or $(C_{2-4})$alkenyl;

$A_1$, $A_2$, $A_3$, and $A_4$ may be identical or different and represent CH or N with the proviso that either $A_1$ or $A_2$ is N, $A_1$ and $A_2$ cannot both be N, and $R_5$ and $R_{10}$ are absent when $A_3$ and $A_4$ are N;

or a pharmaceutically acceptable salt thereof, stereoisomer thereof, or mixture comprising stereoisomers thereof.

2. The compound according to claim 1, where $R_1$, $R_2$, $R_3$, $R_4$, and $R_5$ may be identical or different and represent H, halogen, CN, $NO_2$, $(C_{1-4})$alkyl, $(C_{1-4})$haloalkyl, $(C_{2-4})$alkenyl, OH, $O(C_{1-4})$alkyl, O $(C_{1-4})$haloalkyl, $N(R^A)R^B$, $C(O)N(R^A)R^B$, $C(O)R^A$, $CO_2R^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R_6$, $R_7$, $R_8$, $R_9$, and $R_{10}$ may be identical or different and represent H, CN, $NO_2$, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^B$, $C(O)R^A$, $CO_2R^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R^A$ and $R^B$ may be identical or different and represent H, $(C_{1-4})$alkyl, $(C_{1-4})$ haloalkyl or $(C_{2-4})$alkenyl.

3. The compound according to claim 1, where $A_4$ represents N.

4. The compound according to claim 1, where $R_3$ is CN.

5. The compound according to claim 1, where $R_3$ is CHO.

6. A pharmaceutical composition comprising a therapeutically effective amount of a compound according to claim 1 and one or more pharmaceutically acceptable carrier, excipient, or diluent.

7. A method for the treatment or prophylaxis of a disease selected from the group consisting of HIV infection, hepatocarcinoma, acute lymphoblastic leukemia, cholangiocarcinoma and lung carcinoma comprising administering to a patient in need thereof a dose of the following compound effective to treat or to inhibit the disease:

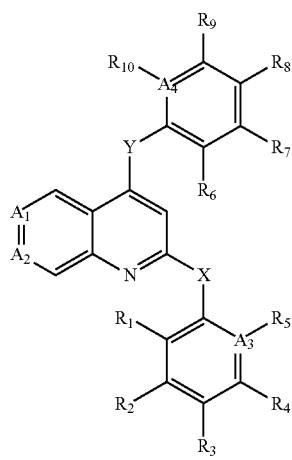

where

X and Y may be identical or different and represent O, NH or S;

$R_1$, $R_2$, $R_3$, $R_4$, $R_5$, $R_6$, $R_7$, $R_8$, $R_9$, and $R_{10}$ may be identical or different and represent H, halogen, CN, $NO_2$, $(C_{1-4})$alkyl, $(C_{1-4})$haloalkyl, $(C_{2-4})$alkenyl, OH, $O(C_{1-4})$alkyl, $O(C_{1-4})$haloalkyl, $N(R^A)R^B$, $C(O)N(R^A)R^B$, $C(O)R^A$, $CO_2R^A$, CHO, $C_{2-4}$ alkenyl substituted with CN, $C_{2-4}$ alkenyl substituted with COOH, $C_{2-4}$ alkenyl substituted with CHO, or $C_{2-4}$ alkenyl substituted with OH;

$R^A$ and $R^B$ may be identical or different and represent H, $(C_{1-4})$alkyl, $(C_{1-4})$haloalkyl, or $(C_{2-4})$alkenyl;

$A_1$, $A_2$, $A_3$, and $A_4$ may be identical or different and represent CH or N with the proviso that $A_1$ and $A_2$ cannot both be N, that $R_5$ and $R_{10}$ are absent when $A_3$ and $A_4$ are N;

or a pharmaceutically acceptable salt thereof, stereoisomer thereof, or mixture comprising stereoisomers thereof.

8. The method according to claim 7, wherein the disease is hepatocarcinoma, acute lymphoblastic leukemia, cholangiocarcinoma or lung carcinoma.

9. The method according to claim 7, wherein the disease is HIV infection and the method comprises administering to the patient an HIV inhibitory dose of the compound in combination with other ARV agent(s).

10. The method according to claim 7, wherein the disease is hepatocarcinoma, acute lymphoblastic leukemia, cholangiocarcinoma or lung carcinoma and the method comprises administering to the patient a cancer inhibitory dose of the compound in combination with radiation and/or other chemotherapeutic agents(s).

11. A compound of the formula (I):

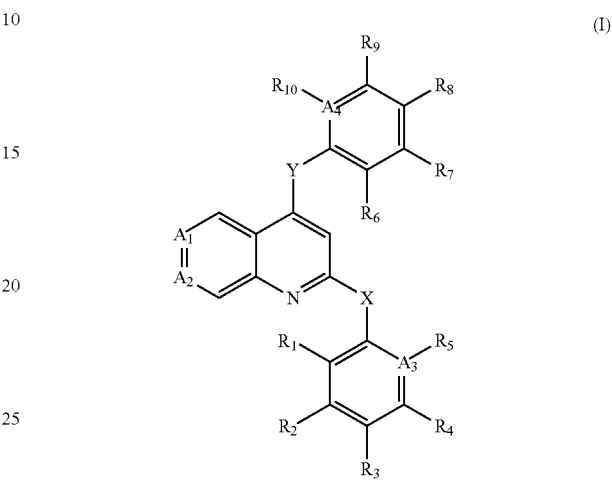

where

X and Y are different and respectively represent O and S, O and NH, NH and S, S and NH, or S and O;

R1, R2, R3, R4, R5, R6, R7, R8, R9, and R10 may be identical or different and represent H, halogen, CN, NO2, (C1-4)alkyl, (C1-4)haloalkyl, (C2-4)alkenyl, OH, O(C1-4)alkyl, O(C1-4)haloalkyl, N(RA)RB, C(O)N(RA)RB, C(O)RA, CO2RA, CHO, C2-4 alkenyl substituted with CN, C2-4 alkenyl substituted with COOH, C2-4 alkenyl substituted with CHO, or C2-4 alkenyl substituted with OH;

RA and RB may be identical or different and represent H, (C1-4)alkyl, (C1-4)haloalkyl, or (C2-4)alkenyl;

A1, A2, A3, and A4 may be identical or different and represent CH or N with the proviso that A1 and A2 cannot both be N, and R5 and R10 are absent when A3 and A4 are N;

or a pharmaceutically acceptable salt thereof, stereoisomer thereof, or a mixture comprising stereoisomers thereof.

12. A pharmaceutical composition comprising a therapeutically effective amount of a compound according to claim 11 and one or more pharmaceutically acceptable carrier, excipient, or diluent.

13. A method for the treatment or prophylaxis of a disease selected from the group consisting of HIV infection, hepatocarcinoma, acute lymphoblastic leukemia, cholangiocarcinoma and lung carcinoma comprising administering to a patient in need thereof the compound according to claim 1.

14. A method for the treatment or prophylaxis of a disease selected from the group consisting of HIV infection, hepatocarcinoma, acute lymphoblastic leukemia, cholangiocarcinoma and lung carcinoma comprising administering to a patient in need thereof the compound according to claim 11.

* * * * *